United States Patent
Nazzal et al.

(10) Patent No.: US 10,874,635 B2
(45) Date of Patent: Dec. 29, 2020

(54) TOCOTRIENOL COMPOSITIONS

(71) Applicants: Sami Mahmoud Nazzal, Monroe, LA (US); Paul W. Sylvester, West Monroe, LA (US); Alaadin Y. Alayoubi, Monroe, LA (US)

(72) Inventors: Sami Mahmoud Nazzal, Monroe, LA (US); Paul W. Sylvester, West Monroe, LA (US); Alaadin Y. Alayoubi, Monroe, LA (US)

(73) Assignee: First Tech International Limited, Beijing (CN)

( * ) Notice: Subject to any disclaimer, the term of this patent is extended or adjusted under 35 U.S.C. 154(b) by 0 days.

(21) Appl. No.: 13/656,573

(22) Filed: Oct. 19, 2012

(65) Prior Publication Data

US 2013/0101644 A1 Apr. 25, 2013

Related U.S. Application Data

(60) Provisional application No. 61/667,489, filed on Jul. 3, 2012, provisional application No. 61/550,009, filed on Oct. 21, 2011.

(51) Int. Cl.
*A61K 31/355* (2006.01)
*A61K 9/107* (2006.01)

(52) U.S. Cl.
CPC .......... *A61K 31/355* (2013.01); *A61K 9/1075* (2013.01)

(58) Field of Classification Search
CPC ............................ A61K 31/355; A61K 9/1075
See application file for complete search history.

(56) References Cited

U.S. PATENT DOCUMENTS

| | | | | |
|---|---|---|---|---|
| 5,821,264 A * | 10/1998 | Lane et al. | | 514/458 |
| 6,596,306 B1 * | 7/2003 | Ho et al. | | 424/450 |
| 2002/0032171 A1 | 3/2002 | Chen et al. | | |
| 2003/0059470 A1 * | 3/2003 | Muller | | 424/489 |
| 2004/0043043 A1 | 3/2004 | Schlyter et al. | | |
| 2006/0014788 A1 | 1/2006 | Gumkowski | | |
| 2007/0104780 A1 * | 5/2007 | Lipari et al. | | 424/456 |
| 2009/0004262 A1 * | 1/2009 | Shaw et al. | | 424/456 |
| 2010/0166918 A1 | 7/2010 | Miller | | |
| 2010/0292316 A1 | 11/2010 | Sanders et al. | | |
| 2011/0045050 A1 | 2/2011 | Elbayoumi | | |
| 2011/0052704 A1 | 3/2011 | Nazzal et al. | | |

FOREIGN PATENT DOCUMENTS

| | | |
|---|---|---|
| EP | 1170003 A1 | 1/2002 |
| WO | 97/03651 A1 | 2/1997 |
| WO | 02/26324 A2 | 4/2002 |

OTHER PUBLICATIONS

Tang et al., Self-Emulsifying Drug Delivery Systems: Strategy for Improving Oral Delivery of Poorly Soluble Drugs, Current Drug Therapy, abstract, 2007, vol. 2, p. 85-93, Bentham Science Publishers Ltd.

International Search Report and Written Opinion for related PCT application PCT/US2012/061198 dated Dec. 28, 2012.

Sylvester, Paul et al., The Value of Tocotrienols in the Prevention and Treatment of Cancer, Journal of the American College of Nutrition, 2010, vol. 29, No. 3, Supplement.

Hazem, Ali et al., Comparison between lipolysis and compendial dissolution as alternative techniques for the in vitro characterization of alpha-tocopherol self-emulsified drug delivery systems (SEDDS), Oct. 26, 2007, International Journal of Pharmaceutics 352 (2008) 104-114.

European Patent Office Search Report for application No. 12841429.9 dated Apr. 8, 2015 that application being a related application.

Julianto, Improved Bioavailability of vitamin E with a Self Emulsifying Formulation, International Journal of Pharmaceutics, Elsevier, vol. 200, No. 1, Jan. 1, 2000, pp. 53-57.

* cited by examiner

*Primary Examiner* — Sean M Basquill
(74) *Attorney, Agent, or Firm* — John B. Edel; Edel Patents LLC

(57) ABSTRACT

Vitamin E compositions, methods of making such compositions and therapeutic uses of vitamin E compositions are disclosed. Compositions of matter comprising a tocotrienol making up at least 15 dry basis weight percent of the composition of matter and a constituent selected from a triglyceride and a triglyceride ester, wherein upon mixing of the composition of matter with water the tocotrienol based composition is substantially emulsified; and wherein upon mixing of the composition of matter with water a resulting emulsion has an intensity-weighed mean droplet size of less than 700 nm are also disclosed.

20 Claims, 32 Drawing Sheets

| Trial No. | TRF (% w/w) | Crem (% w/w) | Lab (% w/w) | Cap (% w/w) | Eth (% w/w) | Diss (%) | Load (%) | Size (nm) | Mem. Value |
|---|---|---|---|---|---|---|---|---|---|
| 1 | 0.0 | 0.0 | 0.0 | 0.0 | 100.0 | -- | -- | -- | -- |
| 2 | 0.0 | 40.7 | 40.7 | 7.2 | 11.4 | -- | -- | -- | -- |
| 3 | 84.3 | 0.0 | 0.0 | 6.1 | 9.6 | -- | -- | -- | -- |
| 4 | 71.1 | 0.0 | 28.9 | 0.0 | 0.0 | -- | -- | -- | -- |
| 5 | 65.7 | 26.8 | 0.0 | 0.0 | 7.5 | 25.5 | 65.7 | 5756 | 0.48914 |
| 6 | 0.0 | 85.0 | 0.0 | 15.0 | 0.0 | -- | -- | -- | -- |
| 7 | 74.4 | -5.0 | 20.2 | -0.9 | 11.3 | -- | -- | -- | -- |
| 8 | 39.4 | 37.4 | 10.7 | 6.6 | 6.0 | -- | -- | -- | -- |
| 9 | 59.0 | 19.7 | 16.0 | 3.5 | 1.8 | 80.6 | 59 | 195.5 | 0.88976 |
| 10 | 60.0 | 20.0 | 16.3 | 3.5 | 0.1 | 66.6 | 60 | 203 | 0.80958 |
| 11 | 65.6 | 9.9 | 17.8 | 1.8 | 4.9 | 51.6 | 65.6 | 16783 | 0.65287 |
| 12 | 95.4 | 0.8 | 2.2 | 0.1 | 1.5 | -- | -- | -- | -- |
| 13 | 42.5 | 22.9 | 23.6 | 4.1 | 7.0 | -- | -- | -- | -- |
| 14 | 49.3 | 24 | 25.7 | -0.2 | 1.3 | -- | -- | -- | -- |
| 15 | 70.6 | 9.4 | 10.1 | 3.6 | 6.3 | 5.9 | 70.6 | 36800 | 0.19383 |
| 16 | 80.1 | 7.9 | 9.3 | 0.6 | 2.2 | -- | -- | -- | -- |
| 17 | 55.6 | 17.7 | 18.6 | 2.8 | 5.3 | 100 | 55.6 | 166 | 0.98835 |
| 18 | 57.9 | 27.1 | 3.0 | 3.9 | 8.1 | 84.5 | 57.9 | 209 | 0.91027 |
| 19 | 54.8 | 26.4 | 12.2 | 1.9 | 4.8 | 89.9 | 54.8 | 163.2 | 0.93665 |
| 5 REV | 65.7 | 26.8 | 0.0 | 0.0 | 7.5 | 25.5 | 65.7 | 5756 | 0.48914 |
| 20 | 54.7 | 16.9 | 20.7 | 4.3 | 3.5 | 100 | 54.7 | 162.5 | 0.98751 |
| 21 | 47.4 | 32.9 | 10.6 | 4.9 | 4.3 | -- | -- | -- | -- |
| 9 REV | 59.0 | 19.7 | 16.0 | 3.5 | 1.8 | 79 | 59 | 201.3 | 0.88090 |
| 22 | 60.9 | 15.8 | 15.9 | 2.6 | 4.8 | 31 | 60.9 | 1922 | 0.54886 |
| 23 | 54.3 | 22.1 | 12.1 | 2.8 | 8.6 | 100 | 54.3 | 167 | 0.98705 |
| 24 | 50.0 | 28.2 | 10.8 | 3.8 | 7.2 | 100 | 50.1 | 129 | 0.96893 |
| 25 | 58.1 | 19.0 | 14.7 | 2.9 | 5.4 | 79 | 58.1 | 200 | 0.88045 |
| 26 | 53.1 | 14.1 | 27.9 | 2.1 | 2.9 | 100 | 53.1 | 156.4 | 0.98549 |

\* Reference value based on a 600 mg SEDDS formulation
\*\* Step size = 200% of the reference value

Fig. 3

| Independent factors | Low Level (-1) | High Level (1) |
|---|---|---|
| $X_1$: Homogenization Pressure (psi) X 1000 | 5 | 25 |
| $X_2$: Number of Cycles | 5 | 25 |
| $X_3$: Lipoid® E80 S (% w/w) | 1.2 | 2.4 |
| $X_4$: Tween® 80 (% w/w) | 0.5 | 2 |
| $X_5$: Cholesterol (% w/w) | 0 | 0.5 |
| $X_6$: % Vitamin E in the Oil Phase (% w/w) | 30 | 70 |
| $X_7$: % Oil Phase in the Emulsion (% w/w) | 10 | 20 |
| $X_8$: Temperature during high shear homogenization (°C) | 25 | 70 |

Dependent factors (responses)
$Y_1$: Particle size (nm)
$Y_2$: Polydispersity Index (PI)
$Y_3$: % Vitamin E remaining emulsified after 48 hours of storage
$Y_4$: The temperature of the emulsion at the end of the homogenization run (°C)

Fig. 8

| RUN | Factors (Independent Variable) | | | | | | | | Observed Responses | | | |
|---|---|---|---|---|---|---|---|---|---|---|---|---|
| | $X_1$ | $X_2$ | $X_3$ | $X_4$ | $X_5$ | $X_6$ | $X_7$ | $X_8$ | $Y_1$ | $Y_2$ | $Y_3$ | $Y_4$ |
| 1 | 25 | 25 | 1.2 | 2.0 | 0 | 30 | 10 | 70 | 166 | 0.227 | 100 | 42 |
| 2 | 25 | 5 | 2.4 | 0.5 | 0 | 30 | 20 | 70 | 209 | 0.161 | 100 | 42 |
| 3 | 5 | 5 | 1.2 | 2.0 | 0.5 | 70 | 10 | 70 | 519 | 0.505 | 47 | 31 |
| 4 | 25 | 5 | 2.4 | 2.0 | 0 | 70 | 10 | 25 | 373 | 0.376 | 84 | 41 |
| 5 | 5 | 5 | 1.2 | 0.5 | 0.5 | 30 | 10 | 25 | 324 | 0.317 | 100 | 30 |
| 6 | 5 | 25 | 2.4 | 2.0 | 0.5 | 30 | 20 | 70 | 299 | 0.219 | 100 | 30 |
| 7 | 25 | 5 | 1.2 | 0.5 | 0.5 | 70 | 10 | 70 | 290 | 0.236 | 91 | 53 |
| 8 | 25 | 25 | 2.4 | 0.5 | 0.5 | 70 | 20 | 25 | 342 | 0.337 | 85 | 48 |
| 9 | 5 | 5 | 2.4 | 2.0 | 0 | 30 | 10 | 25 | 274 | 0.224 | 100 | 32 |
| 10 | 5 | 25 | 2.4 | 2.0 | 0.5 | 70 | 20 | 25 | 372 | 0.409 | 62 | 33 |
| 11 | 25 | 25 | 1.2 | 2.0 | 0 | 30 | 20 | 25 | 147 | 0.115 | 100 | 51 |
| 12 | 5 | 25 | 1.2 | 0.5 | 0 | 70 | 20 | 70 | 431 | 0.345 | 69 | 35 |

Fig. 10A

A. Regression equations of the fitted models $Y_1 = 312.17 - 57.67 * X_1 - 32.17 * X_2 - 9.33 * X_3 + 0.50 * X_4 - 0.33 * X_5 + 75.67 * X_6 - 12.17 * X_7 + 6.83 * X_8$
$Y_2 = 0.2893 - 0.0473 * X_1 - 0.0299 * X_2 - 0.0184 * X_3 + 0.0193 * X_4 - 0.0166 * X_5 + 0.0788 * X_6 - 0.0249 * X_7 - 0.0071 * X_8$
$Y_3 = 86.5 + 6.83 * X_1 + 0.5 * X_2 + 3.0 * X_3 - 4.33 * X_4 + 0.667 * X_5 - 13.5 * X_6 - 0.5 * X_7 - 2.0 * X_8$
$Y_4 = 39.0 + 7.167 * X_1 + 2.0 * X_2 - 0.5 * X_3 - 1.0 * X_4 + 1.833 * X_5 + 1.167 * X_6 + 0.833 * X_7 - 0.167 * X_8$ B. Adjusted regression equations at α = 0.1 [showing factors with significant effect on the responses (p<0.1)]

| Source | df[a] | $Y_1$ [Particle size] | | | | $Y_2$ [Polydispersity Index] | | | |
|---|---|---|---|---|---|---|---|---|---|
| | | SOS[b] | MS[c] | F-Ratio | p-Value | SOS[b] | MS[c] | F-Ratio | p-Value |
| $X_1$ | 1 | 39905 | 39905 | 54.21 | 0.005 | 0.0268 | 0.0268 | 14.70 | 0.031 |
| $X_2$ | 1 | 12416 | 12416 | 16.87 | 0.026 | 0.0107 | 0.0107 | 5.89 | 0.093 |
| $X_3$ | 1 | 1045 | 1045 | 1.42 | 0.319 | 0.0041 | 0.0041 | 2.23 | 0.232 |
| $X_4$ | 1 | 3.0 | 3.0 | 0.00 | 0.953 | 0.0045 | 0.0045 | 2.44 | 0.216 |
| $X_5$ | 1 | 1.33 | 1.33 | 0.00 | 0.969 | 0.0033 | 0.0033 | 1.81 | 0.271 |
| $X_6$ | 1 | 68705 | 68705 | 93.34 | 0.002 | 0.0744 | 0.0744 | 40.83 | 0.008 |
| $X_7$ | 1 | 1778 | 1778 | 2.41 | 0.218 | 0.0075 | 0.0075 | 4.09 | 0.136 |
| $X_8$ | 1 | 560 | 560 | 0.76 | 0.447 | 0.0006 | 0.0006 | 0.33 | 0.606 |
| Total error | 3 | 2208 | 736 | | | 0.0055 | 0.0018 | | |
| Total[d] | 11 | 128622 | | | | 0.1373 | | | |

| Source | df[a] | $Y_3$ [% Vit. E remaining emulsified after 48 hours of storage] | | | | $Y_4$ [The temperature of the emulsion at the end of the homogenization run] | | | |
|---|---|---|---|---|---|---|---|---|---|
| | | SOS[b] | MS[c] | F-Ratio | p-Value | SOS[b] | MS[c] | F-Ratio | p-Value |
| $X_1$ | 1 | 560 | 560 | 3.74 | 0.148 | 818.33 | 818.33 | 72.99 | 0.003 |
| $X_2$ | 1 | 3 | 3 | 0.02 | 0.896 | 48.00 | 48.00 | 5.68 | 0.097 |
| $X_3$ | 1 | 108 | 108 | 0.458 | 0.458 | 3.00 | 3.00 | 0.36 | 0.593 |
| $X_4$ | 1 | 225 | 225 | 1.51 | 0.307 | 12.00 | 12.00 | 1.42 | 0.319 |
| $X_5$ | 1 | 5 | 5 | 0.04 | 0.862 | 40.33 | 40.33 | 4.78 | 0.117 |
| $X_6$ | 1 | 2187 | 2187 | 14.61 | 0.031 | 16.33 | 16.33 | 1.93 | 0.258 |
| $X_7$ | 1 | 3 | 3 | 0.02 | 0.896 | 8.33 | 8.33 | 0.99 | 0.394 |
| $X_8$ | 1 | 48 | 48 | 0.32 | 0.611 | 0.33 | 0.33 | 0.04 | 0.855 |
| Total error | 3 | 449 | 150 | | | 25.33 | 8.44 | | |
| Total[d] | 11 | 3589 | | | | 770 | | | |

[a]Degrees of Freedom, [b]Sum of Squares, [c]Mean Square, and [d]Total corrected

Fig. 11

TOCOTRIENOL COMPOSITIONS

This application claims the benefit of provisional application No. 61/667,489 filed on Jul. 3, 2012 and entitled "Parenteral Formulations." This application claims the benefit of provisional application No. 61/550,009 filed on Oct. 21, 2011 and entitled "Drug Delivery."

Vitamin E is a group of compounds having eight members, six of which are described by FIG. 1. Compounds and formulations disclosed herein have potential use as pharmaceutical products and may be employed in the treatment of various maladies including cancer and may specifically have uses in the treatment of breast, colon and other related cancers.

Compositions of matter described herein may, for example, comprise a tocotrienol based composition making up at least 15 dry basis weight percent of the composition of matter and a constituent selected from a triglyceride and a triglyceride ester wherein upon mixing of the composition of matter with water the tocotrienol based composition is substantially emulsified and wherein upon mixing of the composition of matter with water a resulting emulsion has an intensity-weighed mean droplet size of less than 700 nm. In a related embodiment the composition of matter further comprises a first emulsifier making up at least 0.25 dry basis weight percent of the composition of matter. In a related embodiment, the composition of matter is an emulsion. In a related embodiment, the first emulsifier is selected from Polysorbate 80 and phospholipid. In a related embodiment, the first emulsifier is Polysorbate 80 and the emulsion further comprises a phospholipid. In a further related embodiment, the constituent is selected from a triglyceride and a triglyceride ester is a medium chain triglyceride. In a further related embodiment, the constituent is selected from a triglyceride and a triglyceride ester is a Caprylic/Capric triglyceride. In a further related embodiment, the constituent is selected from a triglyceride and a triglyceride ester is a coconut oil. In a further related embodiment the composition of matter further comprises cholesterol. In a further related embodiment, the constituent selected from a triglyceride and a triglyceride ester makes up at least five dry basis weight percent of the composition of matter. In a further related embodiment the composition of matter further comprises a first nonionic copolymer. In a further related embodiment the first nonionic copolymer may be a nonionic block copolymer. In a further related embodiment, the first nonionic copolymer may be poloxamer 188. In a further related embodiment, the first nonionic copolymer may make up at least 0.5 weight percent of the composition of matter. In a further related embodiment, the first nonionic copolymer may make up at least 1.0 weight percent of the composition of matter. In a further related embodiment, the first non-ionic copolymer may make up at least 1.5 weight percent of the composition of matter. In a further related embodiment, the first non-ionic copolymer may make up at least 2.5 weight percent of the composition of matter. In a further related embodiment the composition of matter has an oil phase and the tocotrienol based composition may make a up at least 10 weight percent of the oil phase. In a further related embodiment, the tocotrienol based composition makes up at least 20 weight percent of the oil phase. In a further related embodiment, the tocotrienol based composition makes up at least 30 weight percent of the oil phase. In a further related embodiment the oil phase is at least 5 weight percent of the composition of matter. In a further related embodiment, the oil phase is at least 10 weight percent of the composition of matter. In a further related embodiment the composition of matter contains a poloxamer. In a further related embodiment, the composition of matter is not a hemolytic toxin. In a further related embodiment, the composition of matter has growth inhibitory activity against a cell line selected from MCF-7 human mammary adenocarcinoma and SW-620 human colon adenocarcinoma.

In an embodiment related to the above described embodiments, the composition of matter is a self-emulsifying drug delivery system. In a further related embodiment, the above mentioned constituent is a triglyceride ester. In a further related embodiment, the constituent is polyoxyethylated castor oil. In a further related embodiment, the constituent makes up at least 10 dry basis weight percent of the composition of matter. In a further related embodiment, the constituent makes up at least 15 dry basis weight percent of the composition of matter. In a further related embodiment the composition of matter comprises a glycerol ester. In a further related embodiment, the composition of matter comprises a coconut oil. In a further related embodiment, the composition of matter further comprises an alcohol. In a further related embodiment, the alcohol is ethanol. In separate but related further embodiments, the tocotrienol based composition makes up at least 20 dry basis weight percent of the composition of matter; the tocotrienol based composition makes up at least 30 dry basis weight percent of the composition of matter; the tocotrienol based composition makes up at least 40 dry basis weight percent of the composition of matter; and the tocotrienol based composition makes up at least 50 dry basis weight percent of the composition of matter. In a series of separate but related embodiments, upon mixing of the composition of matter with water the resulting emulsion has an intensity-weighed mean droplet size of less than 500 nm, less than 300 nm, and less than 250 nm. In a related embodiment, the tocotrienol based composition is tocotrienol. In a further related embodiment, the tocotrienol based composition is a tocotrienol derivative.

Self-emulsifying drug delivery system described herein may, for example, comprise a tocotrienol based composition making up at least 15 dry basis weight percent of the composition of matter; a polyoxyethylated triglyceride making up at least 10 dry basis weight percent of the self-emulsifying drug delivery system; wherein upon mixing of the self-emulsifying drug delivery system with water the tocotrienol based composition is substantially emulsified; and wherein upon mixing of the self-emulsifying drug delivery system with water a resulting emulsion has an intensity-weighed mean droplet size of less than 700 nm. In a related embodiment, the self-emulsifying drug delivery system further comprises a glycerol ester; a coconut oil; and an alcohol; wherein the polyoxyethylated triglyceride is polyoxyethylated castor oil.

Emulsion described herein may, for example, comprise a tocotrienol based composition making up at least 15 dry basis weight percent of the emulsion; and a medium chain triglyceride; wherein the tocotrienol based composition is substantially emulsified; wherein the emulsion has an intensity-weighed mean droplet size of less than 500 nm. In a related embodiment, the emulsions may further comprise a phospholipid; and a poloxamer; wherein the medium chain triglyceride makes up at least five dry basis weight percent of the emulsion and wherein the emulsion has an oil phase and the tocotrienol based composition makes up at least 20 weight percent of the oil phase.

BRIEF DESCRIPTION OF THE DRAWINGS

FIG. 3 lists emulsion compositions that were evaluated.

FIG. 8 shows the independent and dependent factors associated with Examples 6-10.

FIG. 10A shows test results for compositions prepared based on a variety of composition preparation independent variables.

FIG. 10B shows polynomial equations based on the relationship of the independent and dependent variables.

FIG. 11 shows analysis of variance results based on responses to the independent variables.

EXAMPLES

Example 1

SEDDS Preparation

Two sets of tocotrienol-rich-fraction of palm oil (TRF) self-emulsifying drug delivery system (SEDDS) formulations described in Table 1 below were prepared using Tween 80 or Cremophor EL as the primary surfactant were prepared with increasing concentration of TRF from 12.5 to 70% w/w. Labrasol, Captex 355, and ethanol were added to the SEDDS as co-surfactant, secondary oil, and co-solvent, respectively. The formulations in each group were loaded with increasing concentration of TRF from 12.5 to 70% w/w, while maintaining the ratio between Labrasol, Captex 350, ethanol, and the primary surfactant constant. One gram of each formulation was prepared by thoroughly mixing the pre-weighed SEDDS ingredients in a borosilicate vial at 1,000 rpm for 5 min using a homogenizer sold as the IKA® UltraTurrax T8 mixer by IKA Works Inc., NC, USA.

TABLE 1

| Formula No. | TRF (% w/w) | Cremophor or Tween (% w/w) | Labrasol (% w/w) | Captex 355 (% w/w) | Ethanol (% w/w) |
| --- | --- | --- | --- | --- | --- |
| 1 | 12.5 | 35.6 | 35.6 | 6.3 | 10 |
| 2 | 15 | 34.6 | 34.6 | 6.1 | 9.7 |
| 3 | 17.5 | 33.6 | 33.6 | 5.9 | 9.4 |
| 4 | 20 | 32.6 | 32.6 | 5.8 | 9.1 |
| 5 | 25 | 30.5 | 30.5 | 5.4 | 8.6 |
| 6 | 30 | 28.5 | 28.5 | 5.0 | 8.0 |
| 7 | 35 | 26.5 | 26.5 | 4.7 | 7.4 |
| 8 | 40 | 24.4 | 24.4 | 4.3 | 6.8 |
| 9 | 45 | 22.4 | 22.4 | 4.0 | 6.3 |
| 10 | 50 | 20.4 | 20.4 | 3.6 | 5.7 |
| 11 | 55 | 18.3 | 18.3 | 3.2 | 5.1 |
| 12 | 60 | 16.3 | 16.3 | 2.9 | 4.6 |
| 13 | 70 | 12.2 | 12.2 | 2.2 | 3.4 |

Materials used in Examples 1-5 were as follows: TRF, which contains approximately 30% α-tocopherol and 70% α, γ, and δ-tocotrienols was a gift from Beta Pharmaceutical Ltd (West Perth, Australia). Polyoxyethyleneglycerol 35 triricinoleate is sold as Cremophor® EL and is a polyoxyethylated castor oil and is sometimes referred to herein as "Cremophor" or "PCO," polyoxyethylene sorbitan 20 monooleate sold as Tween® 80 and is referred to herein as Tween 80 and polysorbate 80, triglycerides of caprylic/capric acid sold as Captex® 355 and referred to herein as "Captex" and C8/C10 polyglycolyzed glycerides from coconut oil sold as Labrasol® referred to herein as "Labrasol" were provided by BASF (Mount Olive, N.J., USA), Uniqema (New Castle, Del., USA), Abitec Corporation (Janesville, Wis., USA), and Gattefossé (Saint-Priest, Cedex, France), respectively. Ethyl alcohol USP was purchased from AAPER Alcohol and Chemical Co. (Shelbyville, Ky., USA). Empty hard gelatin capsules (size 0) were provided by Capsugel (Greenwood, S.C., USA). Deionized water was obtained using the NanoPure purification system. All chemicals were used as supplied without further modification. Examples 1-5 and the section following Example 5 may be read together as a teaching embodiments that relate to SEDDS compositions.

Example 2

Dissolution Tests

Figure 1:
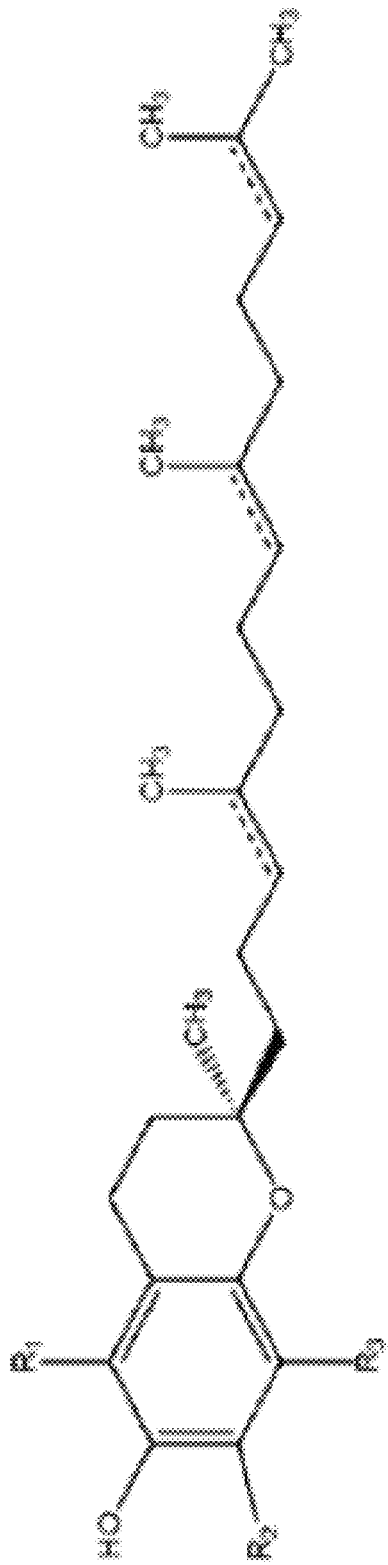
FIG. 1 shows a generic structure of vitamin E.
Figure 2:
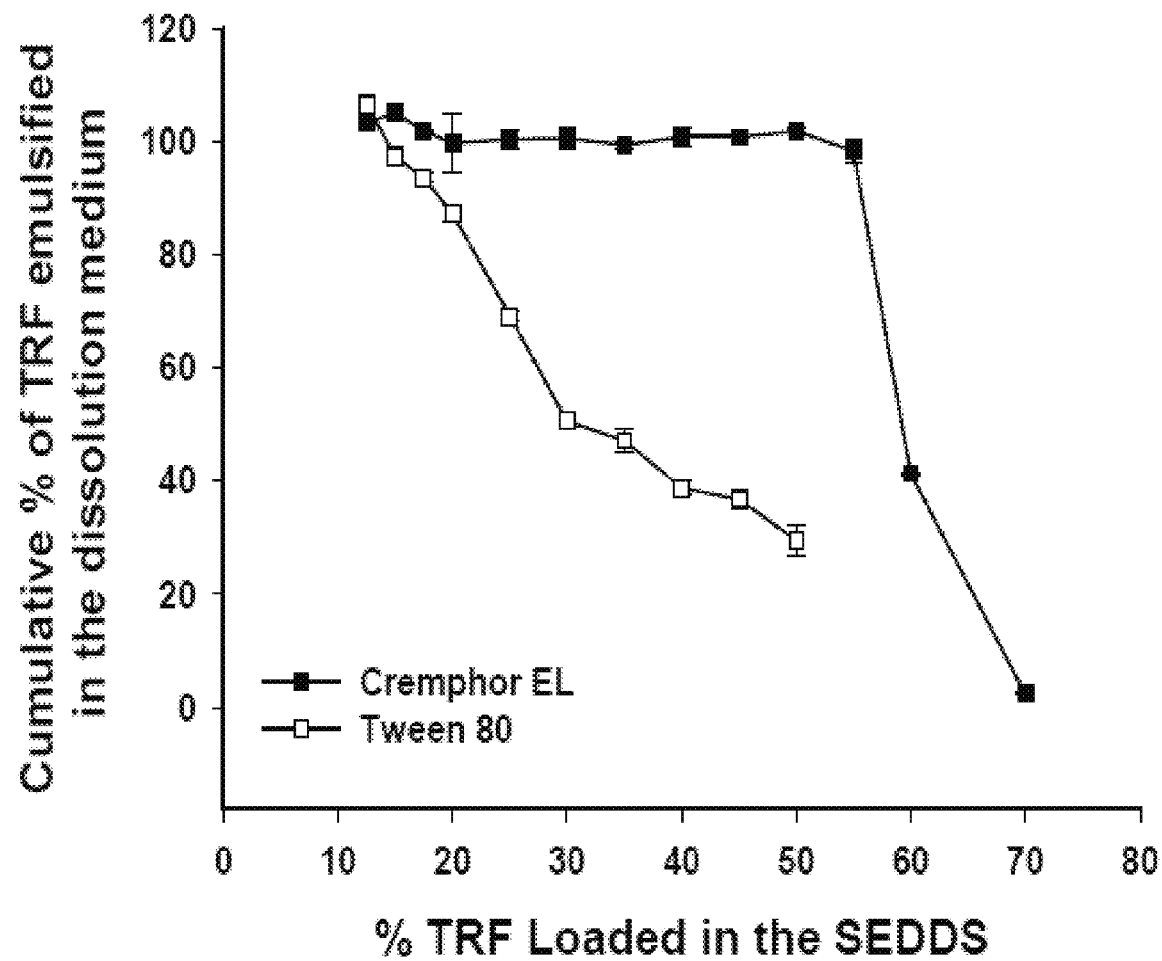
FIG. 2 is a graph showing TRF emulsification percentages for various formulations.

Dissolution experiments were performed in 100 mL deionized water as the dissolution medium using mini USP Type II dissolution apparatus at a paddle speed of 100 rpm and bath temperature of 37±0.5° C. (VK 7000, Varian Inc., NC, USA). In select runs, dissolution vessels were fitted with an ultra-fast fiber-optic probe to monitor the dispersion process. At the beginning of each experiment, size 0 hard gelatin capsule filled with 500 mg of the formulation was released into the dissolution medium. Capsules were held at the bottom of the vessel using stainless-steel sinkers. Dissolution experiments were allowed to run for 15 minutes. At the end of each experiment, a sample was collected to measure the percentage of TRF emulsified and the size of the emulsion droplets in the dissolution medium. The percentage of TRF emulsified was determined spectrophotometrically by measuring the UV absorbance of samples at 295 nm (Cary 50 probe UV/Vis spectrophotometer, Varian Inc., NC, USA). Samples for UV analysis were prepared by first diluting 100 µL of the sample collected from the dissolution medium with 4 mL methanol. Then, 100 µL of this blend was diluted to a final volume of 2 mL with methanol to obtain a clear solution. Intensity-weighed mean droplet size and population distribution (polydispersity index, PI) of the emulsion were measured by photon correlation spectroscopy (PCS) at 23° C. and a fixed angle of 90° using Nicomp™ 380 ZLS submicron particle size analyzer (PSS Inc., Santa Barbara, Calif., USA). When needed, samples for size analysis were diluted with 0.2 mL-filtered and deionized water in order to minimize multiple-particle scattering and to achieve an optimal scattering intensity of 300 KHz. Analyses were performed in triplicates unless otherwise specified. Results associated with Examples 1-5 were obtained by the methods of the present example unless otherwise indicated. The Cumulative percentage of TRF emulsified in dissolution medium as a function of the percentage of TRF loaded in either Tween or Cremophor SEEDS is shown in FIG. 2.

Example 3

Modeling

Figure 4:
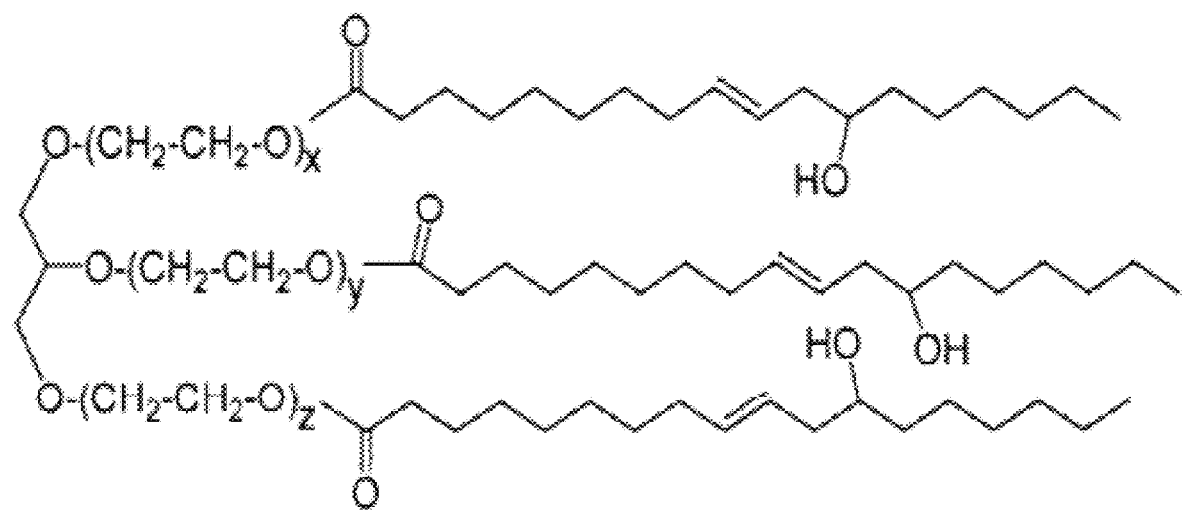
FIG. 4 shows the chemical structure of Polyoxyethyleneglycerol 35 triricinoleate.
Figure 5:
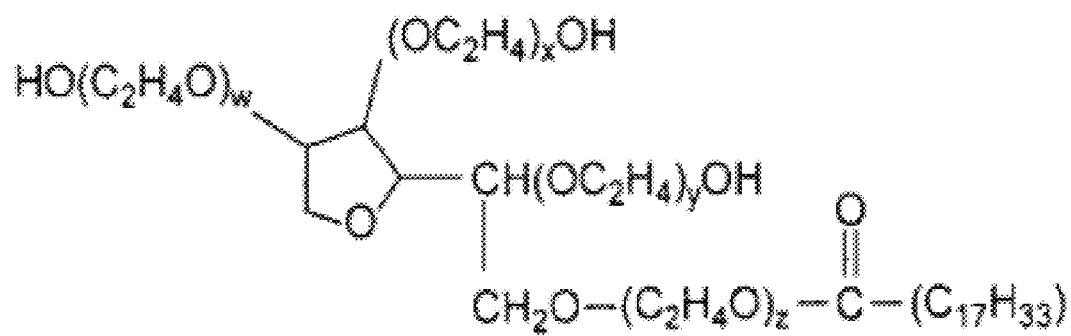
FIG. 5 shows the chemical structure of polyoxyethylene sorbitan 20 monooleate.
Figure 6:
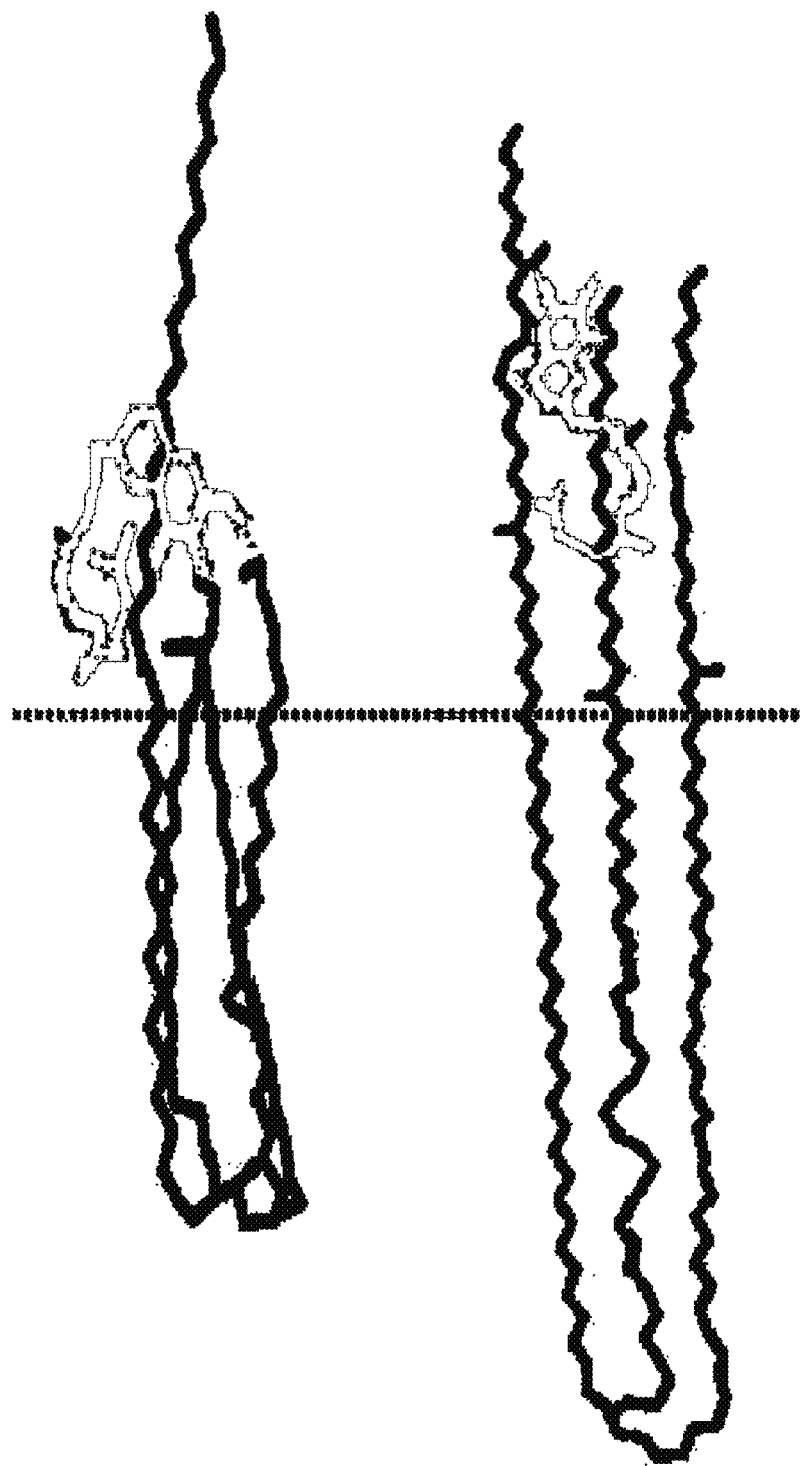
FIG. 6 shows the docking structure of γ-tocotrienol to polysorbate 80 and the docking structure of γ-tocotrienol to Polyoxyethylated castor oil.

Molecules of Cremophor EL and Tween 80 were built using Insight II molecular modelling software available from Accelrys Inc. San Diego, Calif., USA and were energy minimized to obtain the optimized structures. Chemically, Cremophor EL is made of three hydrophobic chains that contain oxyethylene groups. The length of each oxyethylene chain can vary depending on the number of oxyethylene groups with $x+y+z=35$, where x, y and z represent the number of oxyethylene groups as described in "The Molecular Basis of Vitamin E Retention: Structure of Human α-Tocopherol Transfer Protein," Meier, R., Tomizaki, T., Schulze-Briese, C., Baumann, U., Stocker, A., 2003, Journal of Molecular Biology 331, 725-734. Molecules with different oxyethylene chain lengths were built. Similarly, for Tween 80, chain lengths with $x+y+z=20$ was used. Crystal structure of α-tocopherol from the structure of human α-tocopherol transfer protein was used to build the molecule of γ-tocotrienol as a representative component of TRF. Double bonds were introduced to the hydrophobic chain of α-tocopherol and a methyl group was replaced by a hydroxyl group in the head group to obtain the 3D structure of γ-tocotrienol. All structures were energy minimized before docking experiments. Docking of γ-tocotrienol to Cremophor EL and Tween 80 molecules was performed by docking software. A grid box of $120\times120\times120$ Å$^3$ was created around Cremophor EL/Tween 80 molecule to cover the entire molecule with fatty acid side chain. One molecule of Cremophor EL/Tween 80 occupied the grid box created. γ-Tocotrienol could be placed anywhere inside the grid box to evaluate the interaction between γ-tocotrienol and Cremophor EL/Tween 80 molecules. Lamarkian genetic algorithm was then used to find the different docked conformations of γ-tocotrienol to Cremophor EL or Tween 80. Detailed analyses of the ligand-receptor interactions were carried out and the final coordinates of the ligand and receptor were saved as protein data bank file format. PyMol software (Schrodinger LLC, Portland, Oreg.) was used for final display of molecules and to analyze the hydrogen bonding interactions. Preliminary docking calculations and analysis of the docking results were performed on a Linux computer. Ten million energy evaluations with 50 runs in docking were performed on a Linux Cluster computer (High performance computing center at Louisiana State University, Baton Rouge, La.) via the Louisiana Optical Network Infrastructure (LONI). Final low-energy docked structures were used as representative structures to show the interaction between γ-tocotrienol and Cremophor EL or Tween 80. FIG. 4 shows the chemical structure of Polyoxyethyleneglycerol 35 triricinoleate where $x+y+z=35$ and FIG. 5 shows the chemical structure of polyoxyethylene sorbitan 20 monooleate where $w+x+y+z=20$. FIG. 6 shows the docking structure of γ-tocotrienol to polysorbate 80 (top) and the docking structure of γ-tocotrienol to Polyoxyethylated castor oil (bottom).

Example 4

Simplex Tests

An embodiment having the ability to emulsify ≥50% w/w TRF into a stable submicron emulsion was sought out through sequential simplex optimization in a manner comparable to the methodology described in "Sequential Simplex Optimization: A Technique for Improving Quality and Productivity in Research," Walters, F., Jr, L., Morgan, S., Deming, S., 1991., Development, and Manufacturing (Chemometrics series). CRC.

Optimization of the TRF-SEDDS formulation was carried out using the modified simplex method to identify a formulation that can emulsify ≥50% w/w TRF into a stable submicron emulsion. Control and response variables including the optimization criteria (reference values, step size, and the upper and lower limits of the desired responses) are given in Table 2 below.

TABLE 2

| | Control variables | | | | |
|---|---|---|---|---|---|
| | TRF (mg) | Cremophor (mg) | Labrasol (mg) | Captex (mg) | Ethanol (mg) |
| Reference value* | 300 | 122.1 | 122.1 | 21.6 | 34.2 |
| Step size** | 600 | 244.2 | 244.2 | 43.2 | 68.4 |

TABLE 2-continued

| | Response variables | | |
|---|---|---|---|
| | Cumulative % TRF emulsified | Particle size (nm) | % TRF loaded in the SEDDS |
| Objective | Target value: 100% | Minimization | Maximization |
| Influence (0-1) | High (1) | High (1) | very low (0.01) |
| Lower limit | 0 | 1 | 50 |
| Upper limit | 101 | 100000 | 100 |

Step size is the range within which control variable are allowed to vary in each step or experiment. Since information is not available on the approximate location of the optimum formulation, a wide step size (200% of the reference values) was used to allow for the evaluation of a larger design space with lower number of experiments or trials. Reference values are the initial formulation composition around which the software adjusts the composition with each subsequent experiment. The composition of the formulations that were evaluated in each trial and the observed responses are given in FIG. 3, with formulations 1-6 representing the starting "simplex" of the sequential simplex optimization process.

In FIG. 3 Crem is Cremophor; Lab is Labrasol; Cap is Captex 355; Eth is ethanol; Diss is the % TRF emulsified in the dissolution medium; Size is the particle size; Mem Value is the Membership Value. In FIG. 3 Trials No. 1, 2, 3, 4, 6, 7, 8, 12, 13, 14, 16 and 21 were considered "impossible" runs and therefore data from these trials were not generated and/or reported (dashed lines). These trials were considered "impossible" due to one or more of the following reasons: (a) the percentage of TRF in the formulation was <50%, which was outside the effective boundaries of the control variables as defined in Table 2, (b) the concentration of any of the ingredients was given in a negative value by the software, and (c) the formulation completely phase separated in dissolution medium and consequently no data could be generated. In FIG. 3 REV is a reevaluation run. These runs were reevaluated to prevent the simplex from being trapped around a false favorable response The exact composition of each SEDDS formulation was specified by the simplex optimization software sold as Multisimplex® software and available from Grabitech Solutions AB, Sweden, which was used to guide the sequential simplex optimization process. Trials that suggested negative control values or when the theoretical percentage of TRF in the formulation was less than 50% were discarded as impossible trials for which no "membership value" was generated. From each trial, droplet size of the emulsion, percentage of TRF emulsified, and the theoretical percentage of TRF in the formulation were used as the response variables. At the conclusion of each experiment, the results from each response were used to calculate the "membership value". Experiments were performed in a stepwise manner and were continued until the optimum conditions as described in Table 2 were reached, i.e. until the membership values were consistently close to 1. The target of the "membership value" and the overall optimization process was to identify a SEDDS composition (if any) with TRF loading ≥50% that could emulsify 100% of the loaded TRF into a <150 nm nanoemulsion. The % TRF loaded into the formulation was specified as both a control and response variable. This was essential in order to force the program to execute the optimization process for only formulations with TRF loading ≥50%.

Formulations in trials number 5 and 11 were loaded with approximately 65% TRF, with trial number 5 having significantly higher concentration of the primary surfactant Cremophor EL. Nonetheless, absence of Labrasol and Captex 350 in trial number 5, in spite of the high concentration of Cremophor EL, led to only 25% TRF emulsification as opposed to 51% in trial number 11. Not wishing to be bound by theory, the inclusion of these secondary components may improve the physical properties of the formulations and the emulsification of TRF. Only formulations/trials with 100% of the TRF emulsified had a "membership value" >0.9. These included trials number 17, 20, 23, 24, 26, with trial number 24 having the lowest droplet size and consequently one of the highest "membership value". Formulation in trial 24 was loaded with 50% TRF and resulted in a high "membership value" (0.969) and a dispersion with a droplet size smaller than the size of the reference formulation, thereby satisfying the requirements of the optimization process. The narrowing gap between the high (desired) and low (undesired) "membership value" with each new experiment reflects the self-learning algorithm of the sequential simplex optimization process that aims to reach the optimum conditions with the smallest number of trials.

Example 5

Secondary Constituent Tests

Tests were conducted to identify the significance of the co-surfactant, co-solvent, and secondary oil on the properties of the SEDDS formulation. Preliminary experiments indicated that a simple binary blend with Cremophor EL is not sufficient to emulsify TRF. The sequential simplex method was used to systematically and sequentially adjust the composition of the SEDDS formulation. The optimization procedure was carried out as described in Example 4 using the parameter outlined in Table 2. The reference formulation composition (starting simplex) was the Cremophor EL SEDDS at 50% TRF loading, which was identified as formula number 10 in Table 1. Although it was shown from the dissolution study that a maximum 55% TRF could be loaded into a Cremophor EL based formulation, 50% TRF loading was selected as the starting simplex to avoid optimizing the formulation around the borderlines and only formulations that can emulsify 100% of the loaded TRF were considered in the optimization process. Table 4 below shows the control and response variables that were used for the construction of the second simplex run.

TABLE 4

| | Control variables | | | |
|---|---|---|---|---|
| | Cremophor (mg) | Labrasol (mg) | Captex (mg) | Ethanol (mg) |
| Reference value* | 122.1 | 122.1 | 21.6 | 34.2 |
| Step size** | 244.2 | 244.2 | 43.2 | 68.4 |

| | Response variables | |
|---|---|---|
| | Cumulative % TRF emulsified | Particle size (nm) |
| Objective | Target value: 100% | Minimization |
| Influence (0-1) | High (1) | High (1) |
| Lower limit | 0 | 1 |
| Upper limit | 101 | 3000 |

*Reference value based on a 600 mg SEDDS formulation
**Step size = 200% of the reference value Formulation compositions that resulted in <100% emulsification were deemed "impossible" and were excluded from the optimization process. For the present experiment, a total of 16 trials were performed, of which 6 were "impossible". Table 5 below shows the composition of the SEDDS and the observed responses for the trials that were performed sequentially as part of the second simplex run.

TABLE 5

| Trial No. | TRF (% w/w) | Crem (% w/w) | Lab (% w/w) | Cap (% w/w) | Eth (% w/w) | Diss (%) | Size (nm) | Mem. Value |
|---|---|---|---|---|---|---|---|---|
| 1 | 50 | 0.0 | 50.0 | 0.0 | 0.0 | — | — | — |
| 2 | 50 | 23.0 | 23.0 | 4.1 | 0.0 | 100 | 132.1 | 0.97790 |
| 3 | 50 | 21.9 | 21.9 | 0.0 | 6.1 | 100 | 131.45 | 0.97801 |
| 4 | 50 | 0.0 | 0.0 | 19.4 | 30.6 | — | — | — |
| 5 | 50 | 50.0 | 0.0 | 0.0 | 0.0 | — | — | — |
| 6 | 50 | 0.0 | 38.3 | 4.5 | 7.2 | — | — | — |
| 7 | 50 | 15.4 | 34.6 | 0.0 | 0.0 | 100 | 207 | 0.96504 |
| 8 | 50 | 19.6 | 24.5 | 2.3 | 3.7 | 100 | 121 | 0.97979 |
| 9 | 50 | 21.4 | 22.0 | 2.5 | 4.0 | 100 | 125.3 | 0.97906 |
| 10 | 50 | 29.5 | 20.5 | 0.0 | 0.0 | 100 | 112 | 0.98132 |
| 11 | 50 | 35.6 | 16.8 | −0.9 | −1.5 | — | — | — |
| 12 | 50 | 33.5 | 8.4 | 3.2 | 5.0 | 100 | 144 | 0.97587 |
| 13 | 50 | 28.4 | 15.7 | 2.3 | 3.6 | 100 | 122 | 0.97962 |
| 14 | 50 | 26.0 | 19.8 | −0.3 | 4.5 | — | — | — |
| 15 | 50 | 24.1 | 21.7 | 2.4 | 1.8 | 100 | 121 | 0.97979 |
| 16 | 50 | 27.1 | 20.3 | 2.5 | 0.2 | 100 | 114 | 0.98098 |

Crem: Cremophor EL;
Lab: Labrasol;
Cap: Captex 355;
Eth: ethanol;
Diss: % TRF emulsified in the dissolution medium;
Size: Mem Value: Membership Value.
Trail No. 1, 4, 5, 6, 11, and 14 were considered "impossible" runs and therefore data from these trials were not generated and/or reported (dashed lines).

As seen from Table 5, the droplet size of the dispersions was within the 112 to 207 range and all the formulations had a "membership value" >0.965. The similarity in droplet size and "membership value" of trials in the second multisimplex run to the results obtained with trial number 24 from the first simplex run may indicate that once a "membership value" close to 1 is attained, no significant changes in the responses would be expected.

SEDDS Formulation

Previously, experiments formulating SEDDS compositions with Tween 80, Labrasol, and α-tocopherol were unable to obtain stable SEDDS compositions with vitamin E content above 12.5%. The variation of surfactants namely substituting Cremophor EL for Tween 80 resulted in a remarkable improvement in retention of TRF. In general, no differences in lag phase and/or emulsification rate were observed between the formulations when the dissolution process was analyzed by real-time spectroscopy. The formulations completely released from the ruptured capsules and dispersed into the dissolution medium within 10 minutes (data not shown).

For Tween 80 based formulations; a significant decrease in % TRF emulsified was observed when TRF was loaded at concentrations above 17.5%. In formulations where the % TRF emulsified was <100%, the emulsion broke and a visible oil layer was seen on the surface of the dissolution medium. In contrast, when Cremophor EL was used as the primary surfactant, it was possible to load the SEDDS formulations with up to 55% TRF with 100% of the drug emulsified in the dissolution medium, which indicated that an increase in TRF loading did not adversely impact the quality of the SEDDS or its capacity to readily emulsify into the dissolution medium, albeit it may have had an impact on droplet size and PI. When Cremophor EL SEDDS were loaded with >55% TRF, however, phase separation was observed and an oily layer was seen on the surface of the dissolution medium. This could be attributed to the coalescence of unstable globules of the emulsion due to a decrease in the amount of surfactant and co-surfactant available at the oil/water interface.

Figure 7:
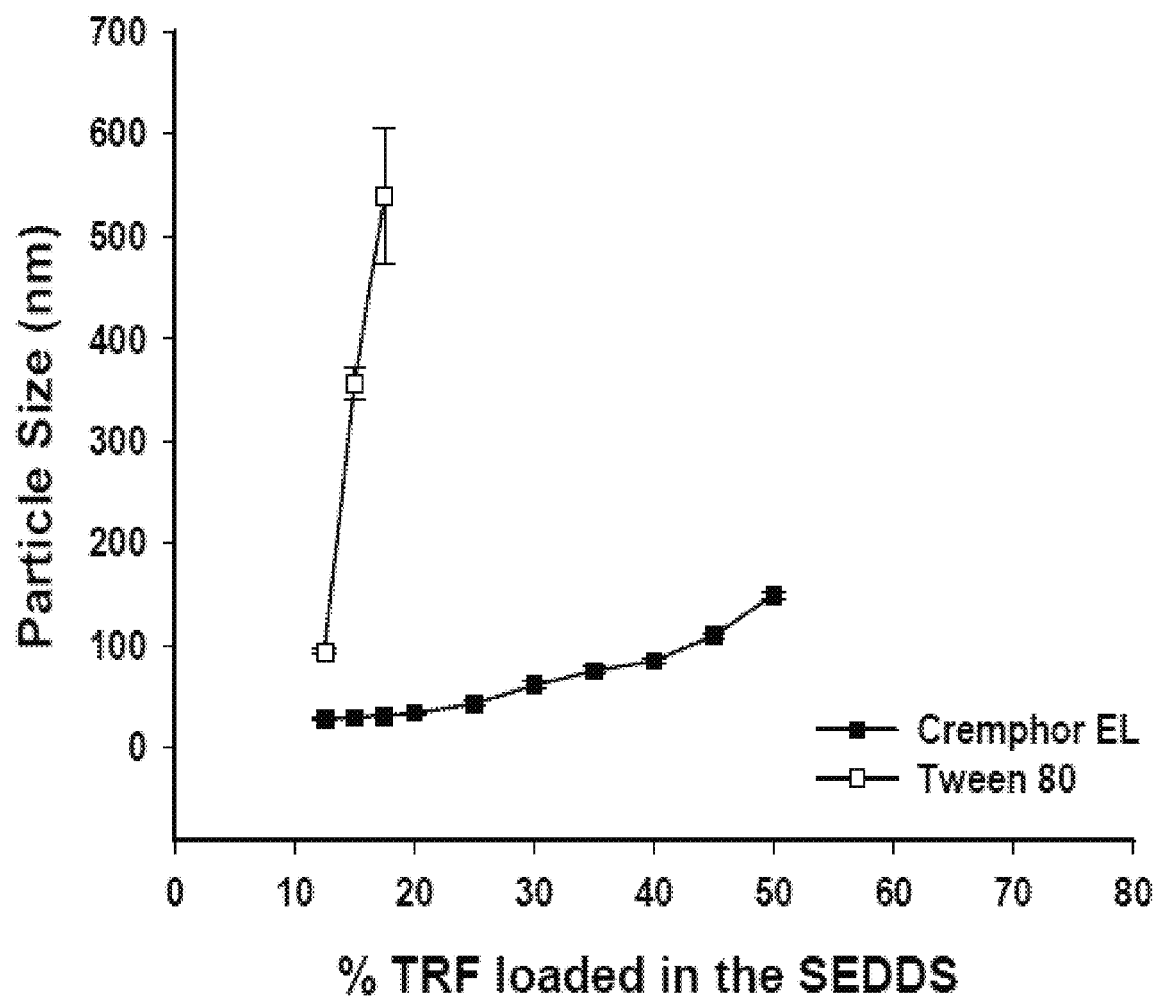
FIG. 7 shows droplet size as a function of TRF loading for two formulations.

Another measure to differentiate between the formulations is the droplet size of the emulsions after SEDDS dispersion into the dissolution medium. In the case of Tween 80 formulations, the droplet size increased significantly with an increase in TRF loading. FIG. 7 shows the change in droplet size of SEDDS formulations using either Tween or Cremophor as the primary surfactant during the initial dissolution studies. The size of the nanoemulsion increased from 100 nm at 12.5% TRF loading to approximately 550 nm at 17.5% TRF loading. Not wishing to be bound by theory, the significant increase in droplet size could be attributed to the positioning of the TRF molecules at the water/emulsion interface. When TRF was loaded at concentrations above 17.5% the droplets coalesced resulting in phase separation. Similarly, a gradual increase in droplet size was observed with Cremophor EL based formulations as the % TRF loaded increased from 12.5 to 50% (FIG. 5A). In contrast to the Tween 80 formulations, however, the size of the dispersions did not exceed 200 nm at the highest TRF concentration.

Another parameter, Polydispersity Index (PI), was used as a measure of the homogeneity and width of the distribution of the emulsion droplets within the medium. While there was a decrease in PI with an increase in TRF loading in the Tween 80 based formulations, the dispersions maintained high PI values (>0.5), which indicated a heterogeneous system with a very broad size distribution. In contrast, PI values for the Cremophor EL based preparations varied with TRF loading. At low TRF loads, the PI did not exceed 0.2, which indicated high degree of homogeneity and narrow droplet size distribution. PI then gradually increased to a maxima of 0.47 at 30% TRF reflecting a heterogeneous system of small and large emulsion droplets. With further increase in TRF loading, the capacity of Cremophor EL to emulsify TRF reached its limit. Consequently and as observed with Tween 80 formulations, the PI decreased as the smaller droplets coalesced to form a homogenous dispersion of larger droplets.

The results of above examples indicate that Cremophor EL is more efficient in emulsifying TRF than Tween 80. Cremophor EL is less hydrophilic (HLB value between 12 and 14) than Tween 80 (HLB=15) and TRF is more hydrophilic than oils, mostly triglycerides that are commonly used as the oil phase in SEDDS formulations. The significant difference in emulsification potential between Cremophor EL and Tween 80, could not be attributed to the difference in their HLB values alone. Not wishing to be bound by theory, structural differences between the two surfactants and their spatial arrangement and positioning in the aqueous media in relation to TRF may play a major role in TRF retention.

While there is a structural resemblance between Cremophor EL shown in FIG. 4 and phospholipids, the presence of a hydroxyl group on the acyl chains may allow the partitioning of TRF within Cremophor EL micelles or emulsion droplets and away from the water/emulsion interface. Docking studies were performed to better understand the differences in emulsifying capacity between Tween 80, and Cremophor EL. In docking studies, the ligand (γ-tocotrienol) was allowed to perform random walks around the receptor (Cremophor or Tween). At each step, the ligand was moved by small increment and orientation, which resulted in different configurations or structure for which interaction energy was calculated with a free-energy expression based on previously defined grid surface. For Cremophor EL, it was observed that most of the low energy structures (−6.25 kcal/mol of docking energy) were formed when the isoprenyl group of γ-tocotrienol was docked near the hydrophobic acyl chains forming a hydrogen bond with the hydroxyl group of Cremophor EL. An example of the potential interaction of Cremophor with the tocotrienol is found in FIG. 6. In the case of Tween 80, low energy structures were obtained when γ-tocotrienol (−3.5 kcal/mol) docked near the interface of oxyethylene moiety and the long hydrophobic chain. Not wishing to be bound by theory, at this configuration, the hydroxyl group of γ-tocotrienol may form a hydrogen bond with the hydroxyl group on the polar head of Tween 80, whereas the isoprenyl group of γ-tocotrienol may form hydrophobic interactions with the hydrophobic acyl chain of Tween 80. Such positioning of γ-tocotrienol at or near the water/emulsion interface may explain the instability of the emulsions and the increase in droplet size with increase in TRF loading. On the other hand, with Cremophor EL, the surfactant molecules may encapsulate TRF within the emulsion droplet and away from the interface, thereby increasing the stability of the emulsion and decreasing its susceptibility to an increase in droplet size with an increase in TRF loading. Not wishing to be bound by theory, the low energy docked structures suggest that γ-tocotrienol binds to Cremophor EL deep inside the hydrophobic pocket whereas in Tween 80 it binds at the interface of the hydrophobic and polar head groups.

Example 6

Emulsion Preparation

Emulsions (15 mL) were prepared by first mixing vitamin E with MCT at 30/70 or 70/30 ratios to form the oil phase. When needed, cholesterol was then dissolved in the oil phase to act as a secondary emulsifier. The primary emulsifiers [Lipoid E80 S and Tween 80] were dispersed in DI water to form the aqueous phase of the emulsion to which glycerol (2.25%, w/w of the total emulsion) was added to adjust tonicity. The concentration of the primary and secondary emulsifiers varied according to the statistical model as given in FIG. 8. The oil and the aqueous phases were heated separately for 5 minutes at the temperature specified by the design for each trial. The two phases were then mixed at 15000 rpm for 2 minutes using an IKA® Ultra-Turrax T8 mixer (IKA® Works Inc., NC, USA) to form the crude pre-emulsion. The final concentration of the oil phase in the emulsions was either 10% or 20% w/w of the total emulsion. A submicron emulsion was obtained by passing the coarse pre-emulsion through a high-pressure homogenizer (EmulsiFlex®-C3, Avestin Inc, Ottawa, Canada) for several cycles and under homogenization pressure predefined by the statistical design. The temperature of the resulting emulsions was measured and the pH was adjusted to a stable pH of 8±0.05 using 0.1 N sodium hydroxide solution.

For Examples 1-5 Vitamin E [(±) [α-Tocopherol] was purchased from Sigma (St. Louis, Mo.). Polyoxyethylenesorbitan mono oleate sold as Tween® 80 referred to herein as Tween 80 was provided by Uniqema (New Castle, Del.). Phospholipids isolated from soybean oil (64-79% phosphatidylcholine and 12-18% phosphatidylethanolamine) sold as Lipoid® E80S and referred to herein as "Lipoid" or "Lipoid E80S" was a generous gift from Lipoid GmbH (Ludwigshafen, Germany). Caprylic/Capric triglyceride a Medium-chain triglyceride sold as Miglyol® 812 referred to herein as MCT or Miglyol a was obtained from Sasol (Witten/Ruhr, Germany). Cholesterol was purchased from Alfa Aesar (Ward Hill, Mass.). Glycerol was purchased from Gallipot, Inc (Saint Paul, Minn.). Double distilled (DI) water was used for all preparations. All chemicals were of reagent grade or higher and were used as supplied without further modification.

Example 7

Emulsion Characterization

Intensity-weighed mean particle size and population distribution (Polydispersity index) of the emulsions were measured by photon correlation spectroscopy (PCS) at 23° C. and a fixed angle of 90° using submicron particle size analyzer available from PSS Inc., Santa Barbara, Calif. and sold as the Nicomp™ 380 ZLS. Polydispersity index (PI), which is a measure of homogeneity and width of the size distribution, ranges from 0, to indicate a monodisperse system, to 0.5, indicating a relatively broad distribution. When needed, samples were diluted with filtered DI water. Analyses were performed in triplicates unless otherwise specified. Short-term stability was assessed by measuring the size and concentration of vitamin E remaining emulsified after storage at ambient conditions for 48 hours. The percentage of vitamin E emulsified was determined by first removing the separated oils from the surface of the emulsion. The content of vitamin E remaining emulsified was then determined by analyzing a sample collected from the bulk of the emulsion spectrophotometrically at 295 nm using a UV spectrophotometer available from Varian Inc., Cary, N.C. and sold as the Cary 50 probe-UV spectrophotometer, after dilution with appropriate amount of methanol.

Example 8

Viscosity Measurement

Viscosity of vitamin E, MCT, and their binary mixtures was measured using an advanced rheometer from TA Instruments Ltd, New Castle, Del. model number AR 2000. A cone and plate geometry was used with a steel plate radius of 40 mm and a cone angle of 2°. The gap between the cone and plate geometry was set at 100 μm. Rheological measurements were made at 23° C. The rheometer was fitted with a Peltier temperature control system, which was monitored during the experiments. For each test, approximately 1 g of vitamin E, MCT, or their binary mixtures was placed between the plates. Preliminary studies were conducted to optimize instrument parameters. Once the system was optimized, a continuous ramp method was used. The shear stress was measured at varying shear rates from 1 to 100 s−1 for a period of 5 minutes. All rheological measurements were carried out in triplicates. Data were analyzed using rheology software namely TA Rheology Advantage software, Version 2.3.

Example 9

Viscosity Test

Figure 9:
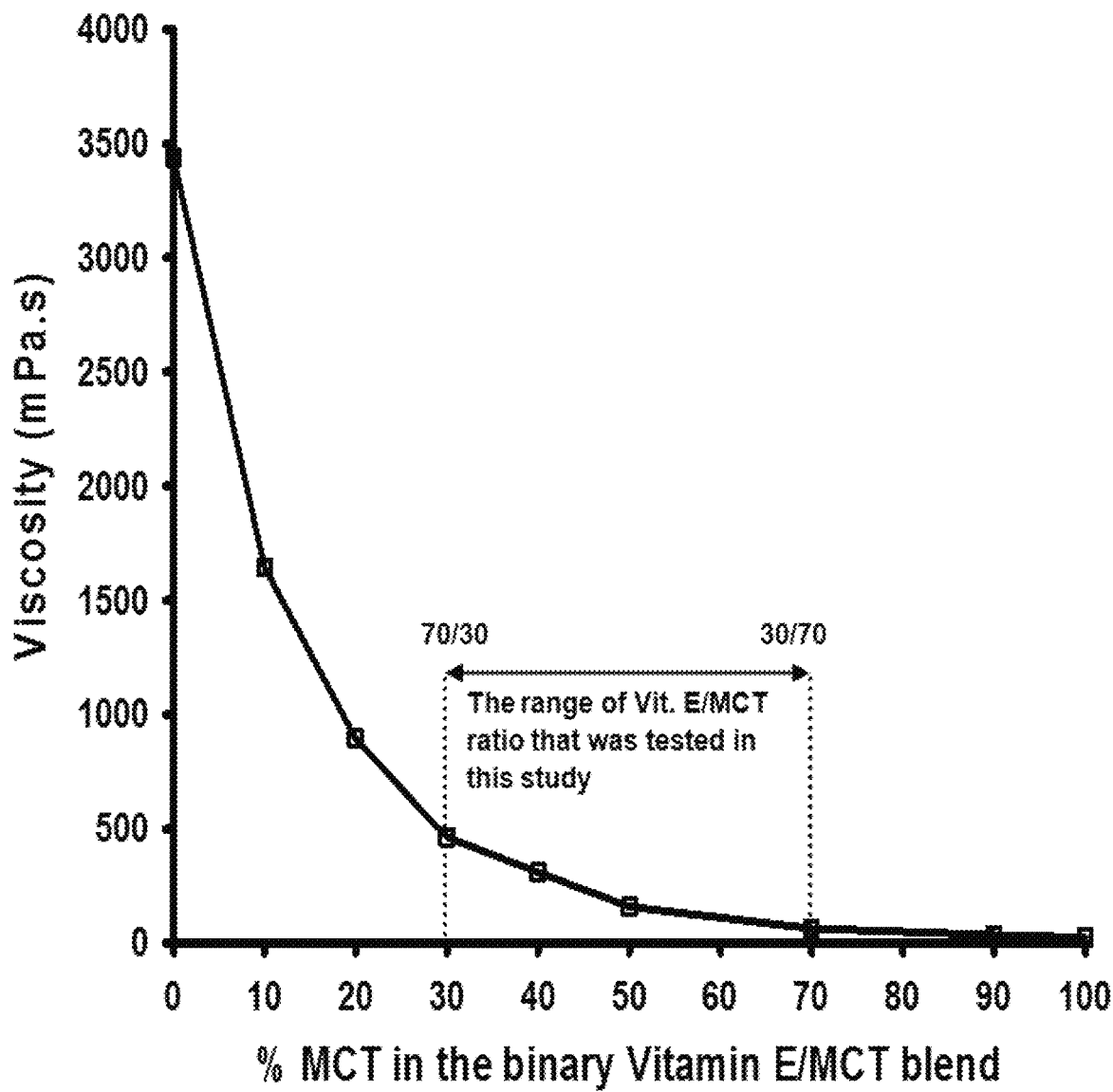
FIG. 9 shows the viscosity profile of the binary blends of vitamin E and MCT.

To demonstrate the impact of MCT, the viscosity of the binary blends was measured at different vitamin E/MCT ratios. FIG. 9 shows the viscosity profile of the binary blends of vitamin E and MCT as a function of % (w/w) MCT in the blend. The viscosity of the blends decreased from a high of 3700 mPa·s for vitamin E alone to a low of 27 mPa·s, which is the viscosity of pure MCT. At the lower end, the viscosity reached a plateau at an approximate ratio of 30/70 for vitamin E/MCT blends. Therefore, two levels of vitamin E loading in the emulsion were evaluated in this study representing a high viscosity system at a 70/30 ratio and a low viscosity system at a 30/70 ratio of vitamin E to MCT. The viscosity of vitamin E was reduced from 3700 at 100% vitamin E to 64 mPa·s at 30% vitamin E by MCT addition.

Example 10

Plackett-Burman Screening

Plackett-Burman screening design is a fractional of a $2^n$ design. Tests associated with the present example were carried out in conjunction with the tests of Examples 6-9. Plackett-Burman screening is frequently used to estimate the main effects when little is known about a system or process. It is also used to correlate independent (factor) and dependent (response) variables using the following polynomial model.

$$Y = A_0 + A_1X_1 + A_2X_2 + A_3X_3 + A_4X_4 + \ldots + A_nX_n$$

In this model, Y is the response, $A_0$ is a constant, and $A_1$-$A_n$ are the coefficients of the independent variables (X). When generating the model and analyzing input data, the Plackett-Burman design ranks the variables based on their magnitude of effect and designates a signs (+ or −) to each effect to indicate whether an increase in the level of each variable has a positive (+) or negative (−) effect on the response. For this study, eight variables were screened in random 12-blocks (runs) for their effect on the quality of vitamin E loaded emulsions. The list of independent variables (X) and their levels, and the monitored responses (Y) are listed in FIG. 8. This design was constructed using statistical software available from Statistical Graphics Corp., Rockville, Md. as STATGRAPHICS Plus software (Version 2.1;).

The upper and lower level of each independent variable [$X_1$-$X_8$] is listed in FIG. 8. These levels were identified in preliminary studies. Also given in FIG. 8 is the list of dependent variables [$Y_1$-$Y_4$] that were evaluated in this study. The exact level of independent variables [$X_1$-$X_8$] and the observed responses [$Y_1$-$Y_4$] for each of the 12 runs are given in FIG. 10A.

The results from FIG. 10A were used to generate polynomial equations for each response as shown in FIG. 10B. Polynomial equations were vital to understand the relationship between the independent and dependent variables. The magnitude and direction of the factor coefficient in each equation was used to explain the nature of factor effect [$X_1$-$X_8$] on the responses [$Y_1$-$Y_4$]. Factors with coefficients of greater magnitude show a high effect on the response. The regression coefficient obtained for $Y_1$, $Y_2$, $Y_3$ and $Y_4$ was 0.98, 0.96, 0.87 respectively and 0.96, which indicates that the model as fitted explains 98%, 96%, 87% and 96% of the variability around the mean, respectively.

By using ANOVA, it was possible to calculate the significance of the ratio of mean square variation due to regression coefficient and residual error. The ANOVA of the model parameters for the response $Y_1$ [particle size] is given in FIG. 11. Three factors [$X_1$, $X_2$ and $X_6$] had p values<0.1, indicating that they had a significant effect on particle size whereas the remaining factors [$X_3$-$X_5$, $X_7$, and $X_8$] had no significant effect on the response. Similar analysis was done for the responses $Y_2$ [polydispersity index, PI], $Y_3$ [% vitamin E that remained emulsified after 48 hours of storage] and $Y_4$ [The temperature of the emulsion at the end of the homogenization run]. The ANOVA of the model parameters for the response $Y_2$ is given in FIG. 11. Three factors, homogenization pressure ($X_1$), Number of cycles ($X_2$) and % vitamin E in oil phase ($X_6$) had a significant (p-value<0.10) effect on this response. For $Y_3$, however, $X_6$ was the only factor that had a significant effect (p-value<0.10) on this response. For the response $Y_4$, two factors $X_1$ and $X_2$ had a significant effect on the temperature of the emulsion at the end of the homogenization run. The statistical significance of the effect of each independent variable on the responses was estimated by analysis of variance (ANOVA). FIGS. 12A-D show the standardized Pareto charts showing the significance ($\alpha$=0.1) of each independent variable (X1-8) on the responses (A) Y1 [Particle size], (B) Y2 [Polydispersity Index], (C) Y3 [% Vitamin E that remained emulsified after 48 hours of storage], (D) Y4 [Emulsion Temperature]. White bars indicate a positive effect while black bars indicate a negative effect on the response. Bars that extend beyond the vertical line indicate a significant effect (p<0.1) of the factor on the response.

Figure 12:
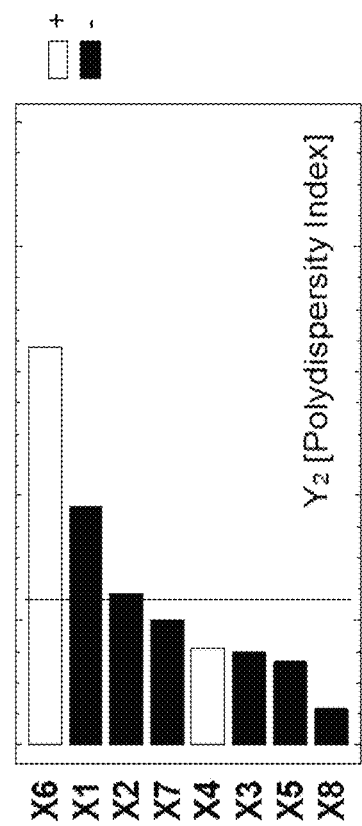
FIGS. 12A-D are Pareto charts showing the significance of independent variables on responses.
Figure 12:
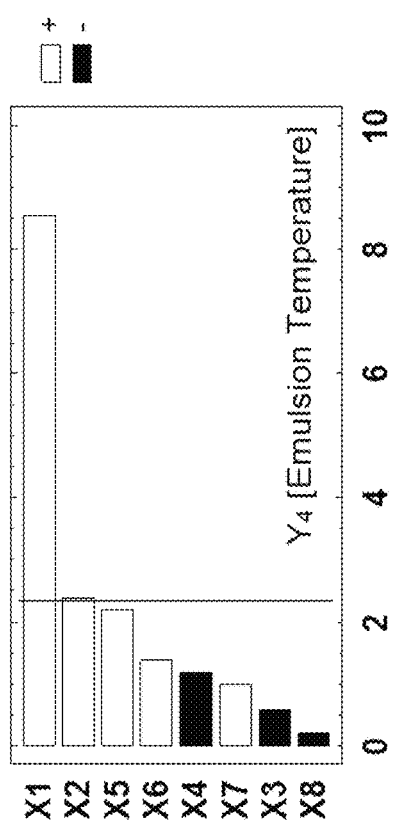
Figure 12:
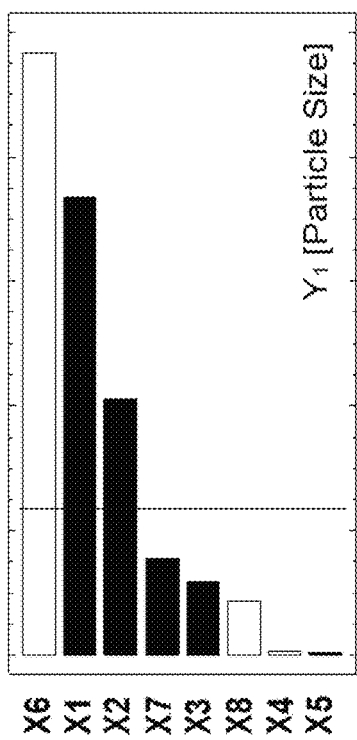
Figure 12:
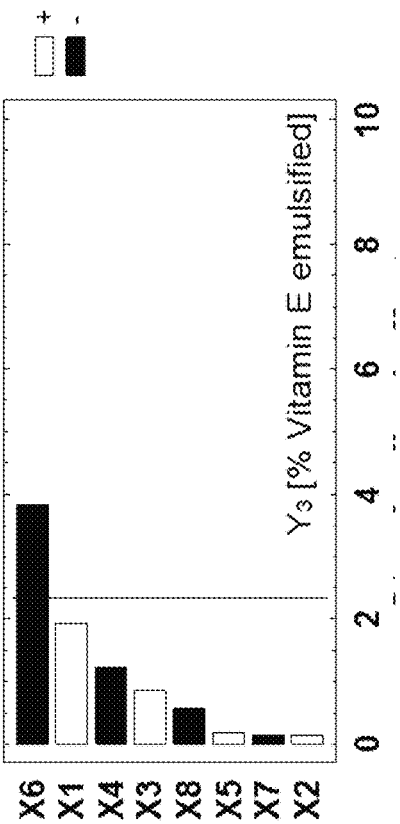
Figure 13:
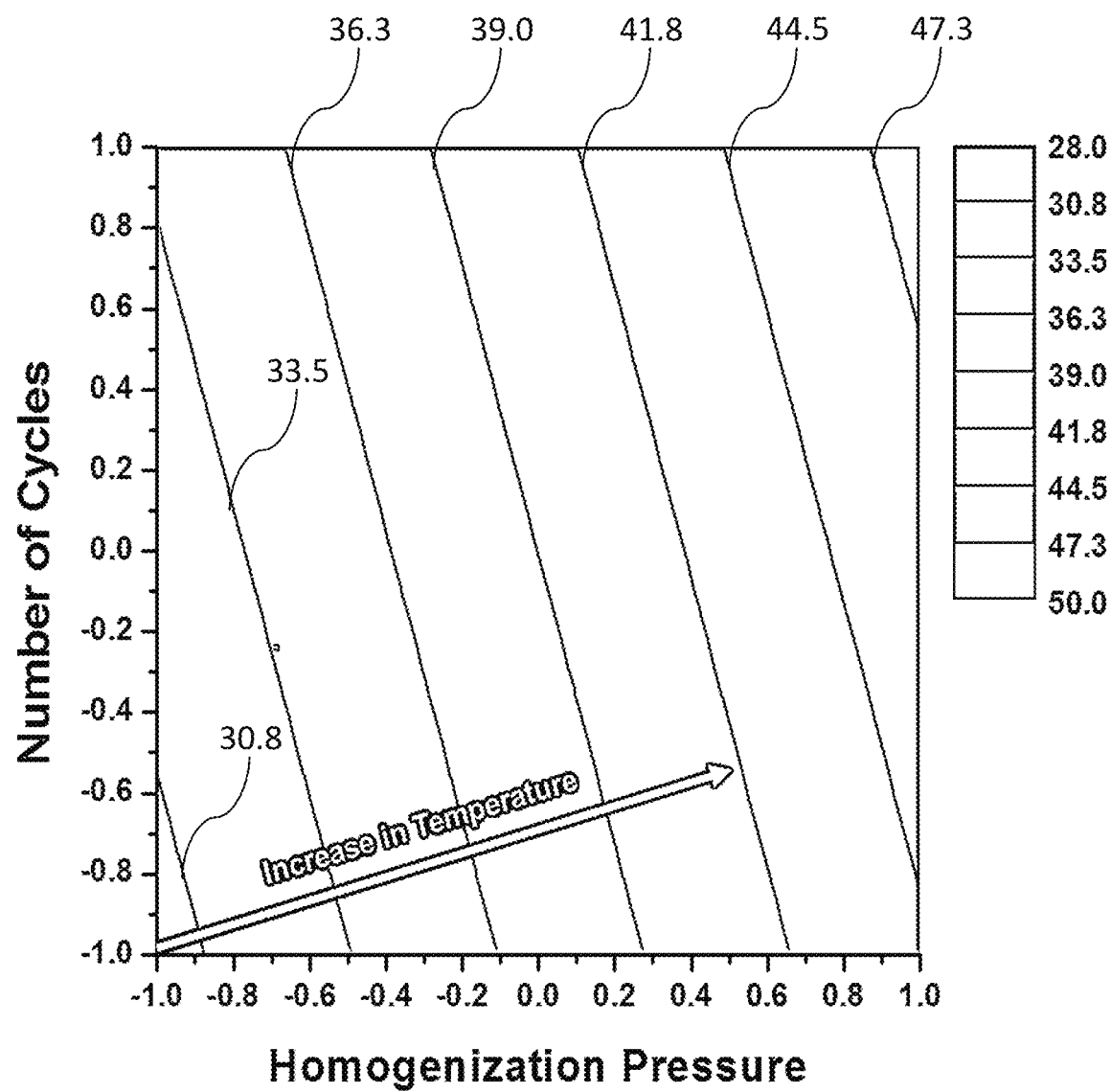
FIG. 13 is a contour plot showing the effects of homogenization pressure and number of cycles on temperature.

Homogenization pressure at two levels, low (5000 psi) and high (25000 psi) was evaluated for its effect on the physical stability of vitamin E emulsions. From the statistical analysis of the results as shown in FIGS. 12A and B and FIG. 11, it could be deduced that an increase in homogenization pressure led to a significant reduction in particle size (Y1) and PI (Y2). A positive correlation was also observed between the temperature of the emulsions at the end of the homogenization run and the applied pressure and the number of cycles. FIG. 13 is a 2D contour plot showing the effects of homogenization pressure (psi) (X1), and number of cycles (X2) on the response Y4 [the temperature of the emulsion at the end of the homogenization run]. Homogenization pressure, however, had an insignificant effect on the % vitamin E that remained emulsified into the aqueous phase of the emulsion after 48 hours of storage.

Increasing the number of cycles improved the physical properties of the emulsion. It significantly reduced particle size and marginally reduced PI. No over processing or instability was observed when the emulsions were processed through 25 cycles. While 25 cycles may be excessive, in certain applications such as the case with viscous lipids, it may be essential. The fact that stable emulsions were obtained is a strong indication that running emulsions through a large number of cycles is acceptable. On the other hand, running the emulsion though only 5 cycles was insufficient to produce stable emulsions as observed by the separation of vitamin E after 48 hours of storage. An interaction effect is expected between homogenization pressure and the number of cycles.

Figure 14:
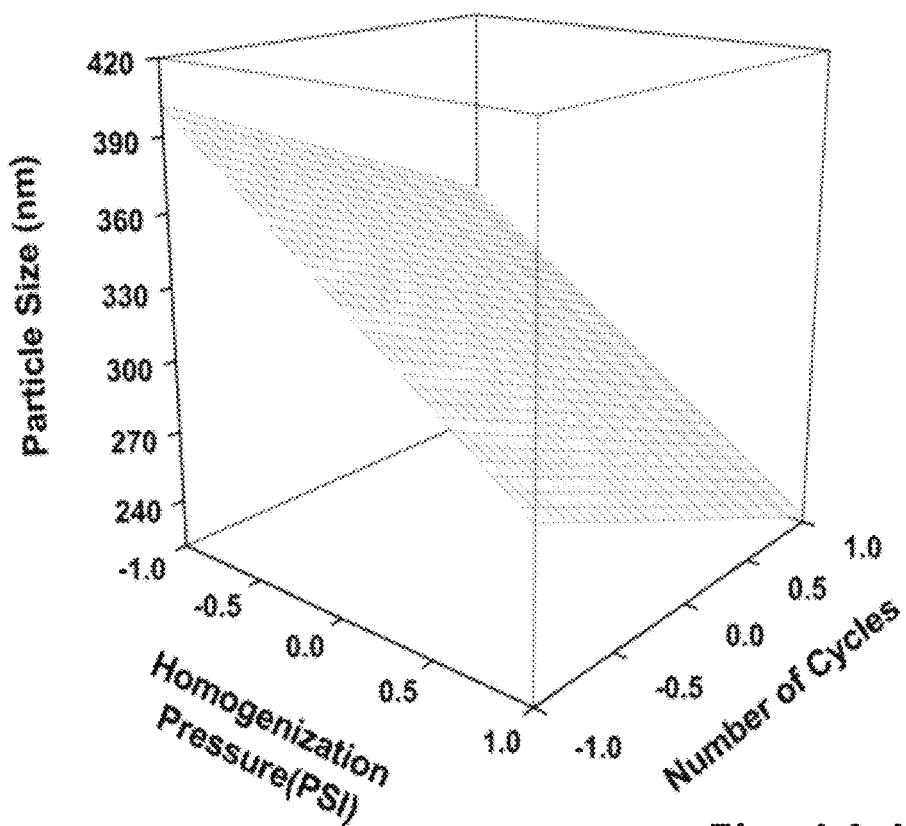
FIG. 14A shows the effective homogenization pressure and number of cycles on particle size.
FIG. 14B shows the effect of oil loading and percentage of vitamin E on particle size.
Figure 14:
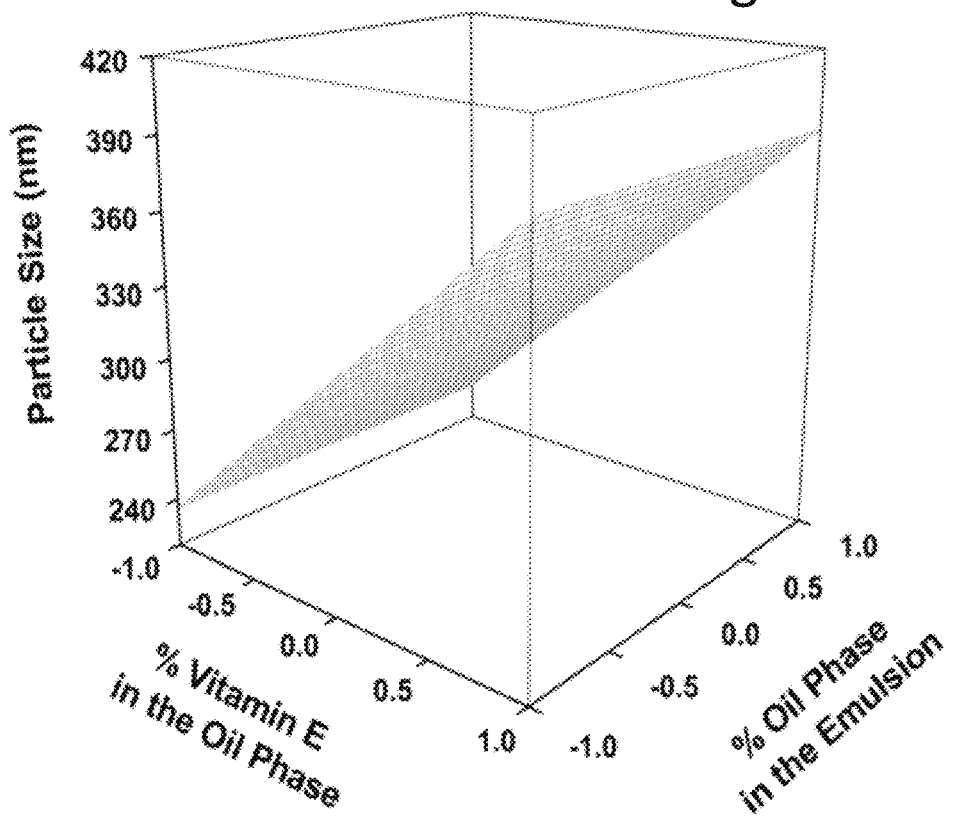

FIGS. 14A and B show 3D response surface plots showing (A) the effect of homogenization pressure (psi) ($X_1$), and number of cycles ($X_2$) on the response $Y_1$ [particle size of the emulsions] and (B) the effect of oil loading in the emulsion and the percentage of vitamin E in the oil phase on the same response ($Y_1$).

Figure 15:
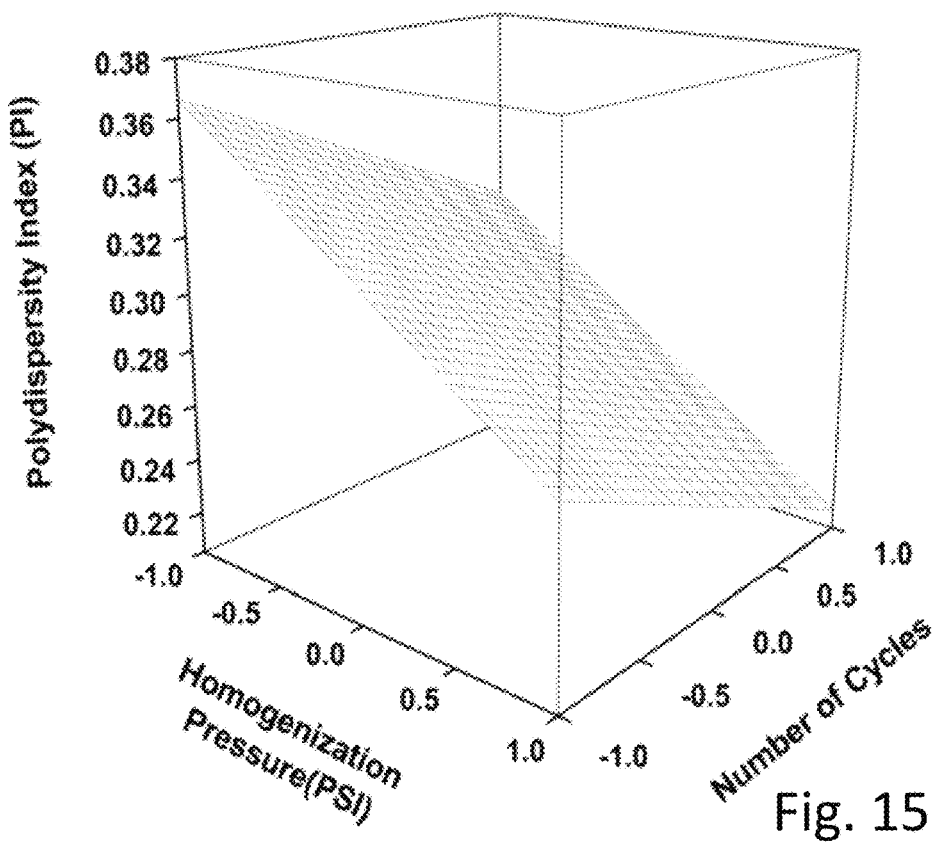
FIG. 15A shows the effective homogenization pressure and number of cycles on polydispersity index.
FIG. 15B shows the effect of oil loading and percentage of vitamin E on polydispersity index.
Figure 15:
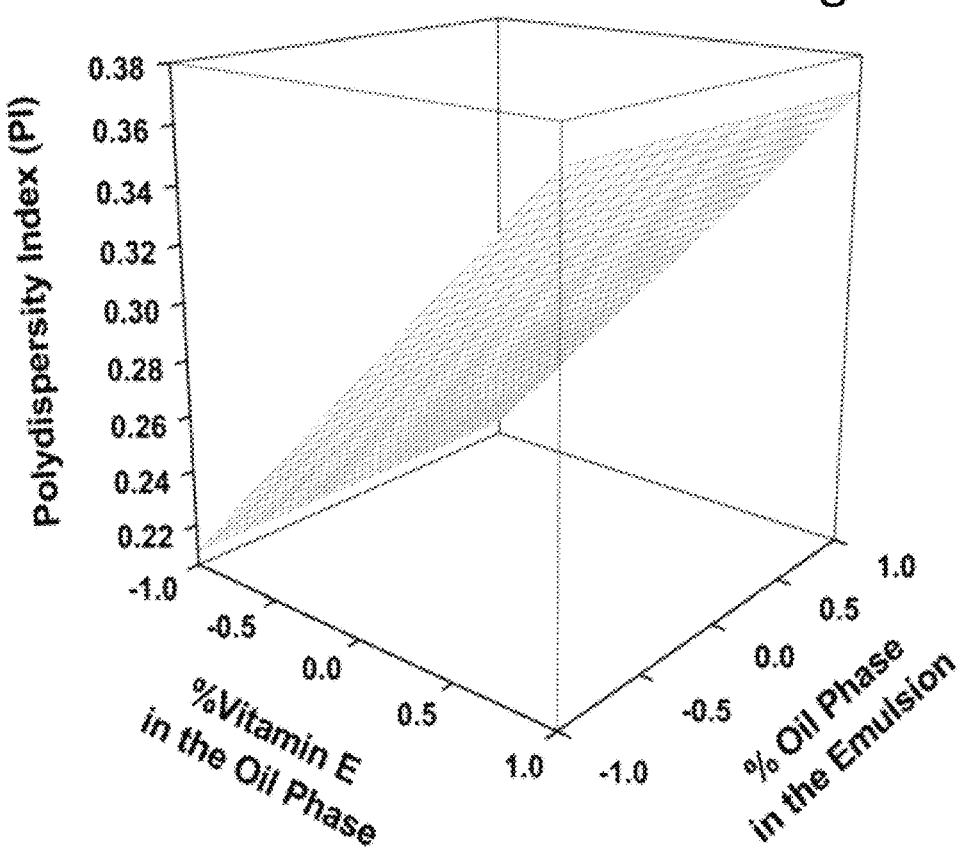

FIGS. 15A and B show 3D response surface plots showing (A) the effect of homogenization pressure (psi) ($X_1$), and number of cycles ($X_2$) on the response $Y_2$ [polydispersity index (PI) of the emulsion] and (B) the effect of oil loading in the emulsion and the percentage of vitamin E in the oil phase on the same response ($Y_2$).

Vitamin E is more polar than LCT and MCT because of the hydroxyl group on the aromatic chromanol ring. Such polarity may result in higher solubility of phospholipids in vitamin E with the result that the emulsifier becomes less available at the vitamin E/water interface. Therefore, Tween 80, a hydrophilic emulsifier with a high HLB value was co-admixed with Lipoid E80S to form the primary emulsifier in this study. The concentration of Tween 80 in the emulsion ranged from 0.5-2% whereas Lipoid E80S was evaluated within a concentration range from 1.2 to 2.4%. Results indicated neither factor had a significant effect on any of the responses. This indicates that vitamin E emulsions 10-20% oil phase could be readily manufactured irrespective of the concentration of the emulsifiers used, as long as the minimum amount of primary emulsifiers was added to the system. This minimum was not more than 1.2% for Lipoid E80S and the minimum was not more than 0.5% Tween 80. Higher concentrations of Lipoid E80S and Tween 80 had no added advantage. In addition, cholesterol had no significant effect on the quality of the emulsions, which might be attributed to the presence of Tween 80, a stronger emulsifier, in the phospholipids layer. It was hypothesized that the hydroxyl group in cholesterol would stabilize the chromanol ring of vitamin E at the water interface. Such effect, however, was insignificant.

Vitamin E to MCT ratio was by far the most significant factor with a profound impact on the quality of the emulsions. Increasing the ratio of vitamin E in the oil phase from 30/70 to 70/30 significantly increased particle size and PI as can be seen in FIGS. 12A and 12B. It also had a negative impact on the stability of the emulsions as measured by the % vitamin E remaining emulsified after 48 hours of storage FIG. 12C. At higher vitamin E ratio, the emulsions broke and a significant portion of vitamin E separated into a visible oily layer on the surface of the emulsion. The negative impact of high vitamin E to MCT ratio could be attributed to its high viscosity and polarity as discussed above.

Figure 16:
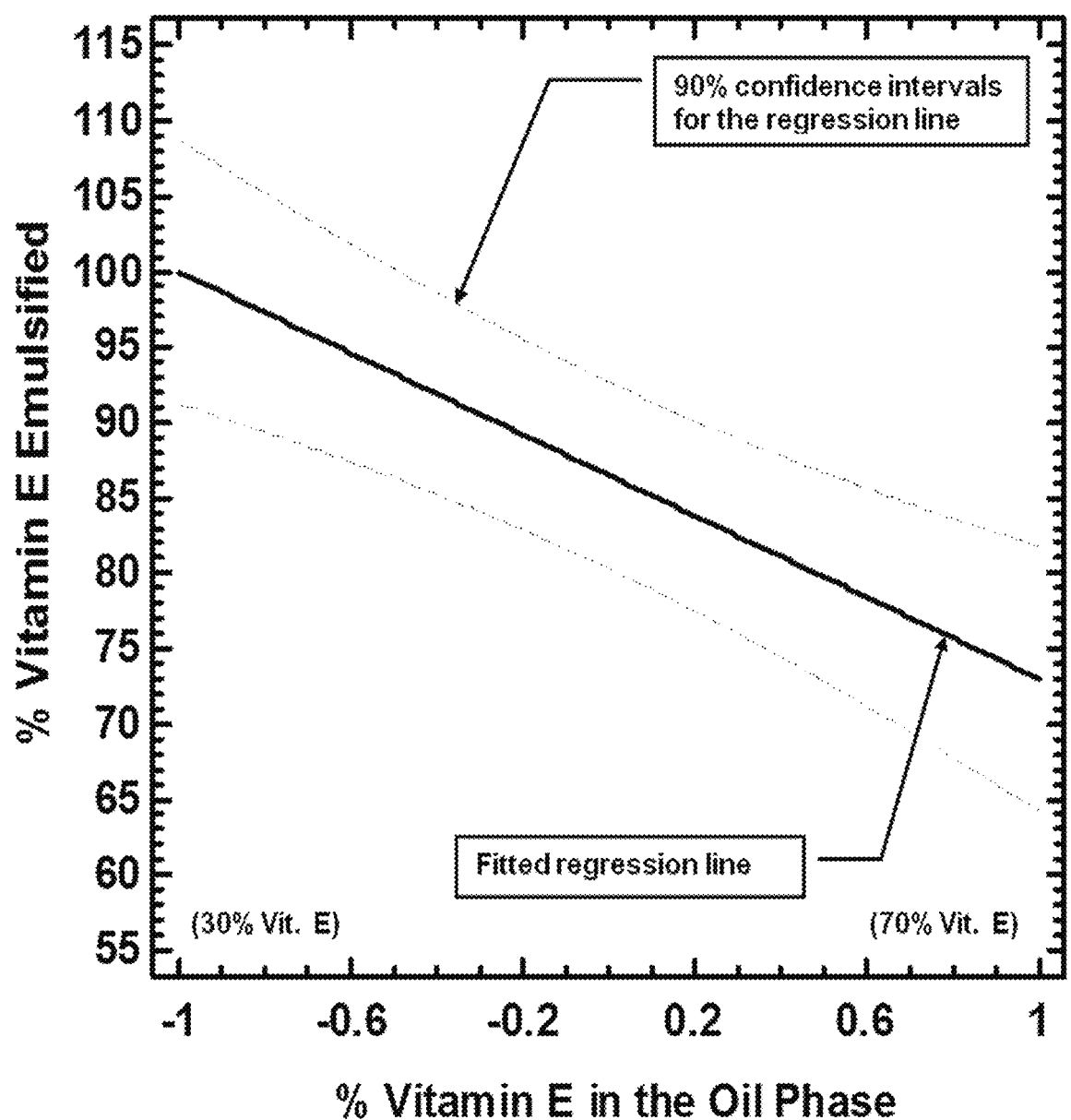
FIG. 16 is a plot showing the effect of vitamin E in the oil phase against vitamin E that remained emulsified.

FIG. 16 shows a linear plot of the fitted model showing the negative effect of the percentage of vitamin E loaded in the oil phase (fraction of the Vit E/MCT blend, $X_6$) on the stability of the emulsions, expressed as the percentage of vitamin E that remained emulsified in water after 48 hours of storage at ambient conditions ($Y_2$).

In general, oil phases with higher viscosities require higher homogenization pressures to achieve smaller particle size distributions, otherwise coarse and unstable large oil size droplets coalesce resulting in a destabilization effect. Not wishing to be bound by theory, because of the higher polarity of vitamin E as compared with MCT, less surfactant will be available at the vitamin E/water interface. Negative effects associated with vitamin E were not observed when the emulsions were loaded with 20% oil phase containing vitamin E and MCT at a ratio of 30/70, which is equivalent to 6% vitamin E of the total emulsion. However, emulsions loaded with 10% oil phase with vitamin E to MCT ratio of 70/30 (equivalent to 7% vitamin E of the total emulsion) were unstable, even in the presence of excess phospholipids. Results of the present example indicate that vitamin E emulsification alone in the absence of secondary low viscosity oil is challenging. Addition of MCT lowered the viscosity of the blend and provided a hydrophobic core to stabilize the oil/water interface. Furthermore, within the range of parameters that were evaluated, only homogenization pressure and number of homogenization cycle seemed to aid in the emulsification of emulsions with high vitamin E to MCT ratio in the oil phase. This could be seen from their significant effect on emulsion stability. Increasing the concentration of primary and secondary surfactants had insignificant effect on the stability of the emulsions. Simply increasing the concentration of these emulsifiers may not improve the quality of the emulsion. Rather, factors other than those evaluated in this study, such as the presence of a ternary emulsifier or a different primary emulsifier altogether may be needed to stabilize the emulsions with high vitamin E to MCT ratio in the oil phase.

Loading emulsions with high concentrations of the oil phase has its advantages. It provides a reservoir to solubilize lipophilic drugs and delivers more energy when used in nutritional applications. High oil concentrations, however, often lead to an increase in particle size and viscosity of the system which in turn may compromise emulsion stability. The increase in particle size may result from an impoverishment of the surfactant at the interface and an increase in the surface tension of the dispersed oil phase. The present example did not indicate a difference between the 10% and 20% emulsion. That is, loading an emulsion with 10% or 20% oil phase while keeping the amount of the other constituents constant resulted in insignificant change in size, PI, or emulsion stability. Excess phospholipids (PL) in emulsions with low oil loading form vesicular PL-rich or TG (triglyceride)-free particles that can induce plasma lipid accumulation in children and adults. Hyperphospholipidemia has been reported in studies of animals, infants, and adults receiving regular 10% MCT/LCT fat emulsions with a PL:TG ratio of 0.12. Therefore, it is essential from a clinical perspective to use the minimum concentration of phospholipids that is sufficient to produce stable parenteral emulsions. While the least concentration of Lipoid E80S could not be identified from the current Plackett-Burman design, it clearly demonstrated that higher concentrations are not necessary beyond what is used in commercial products.

Figure 17:
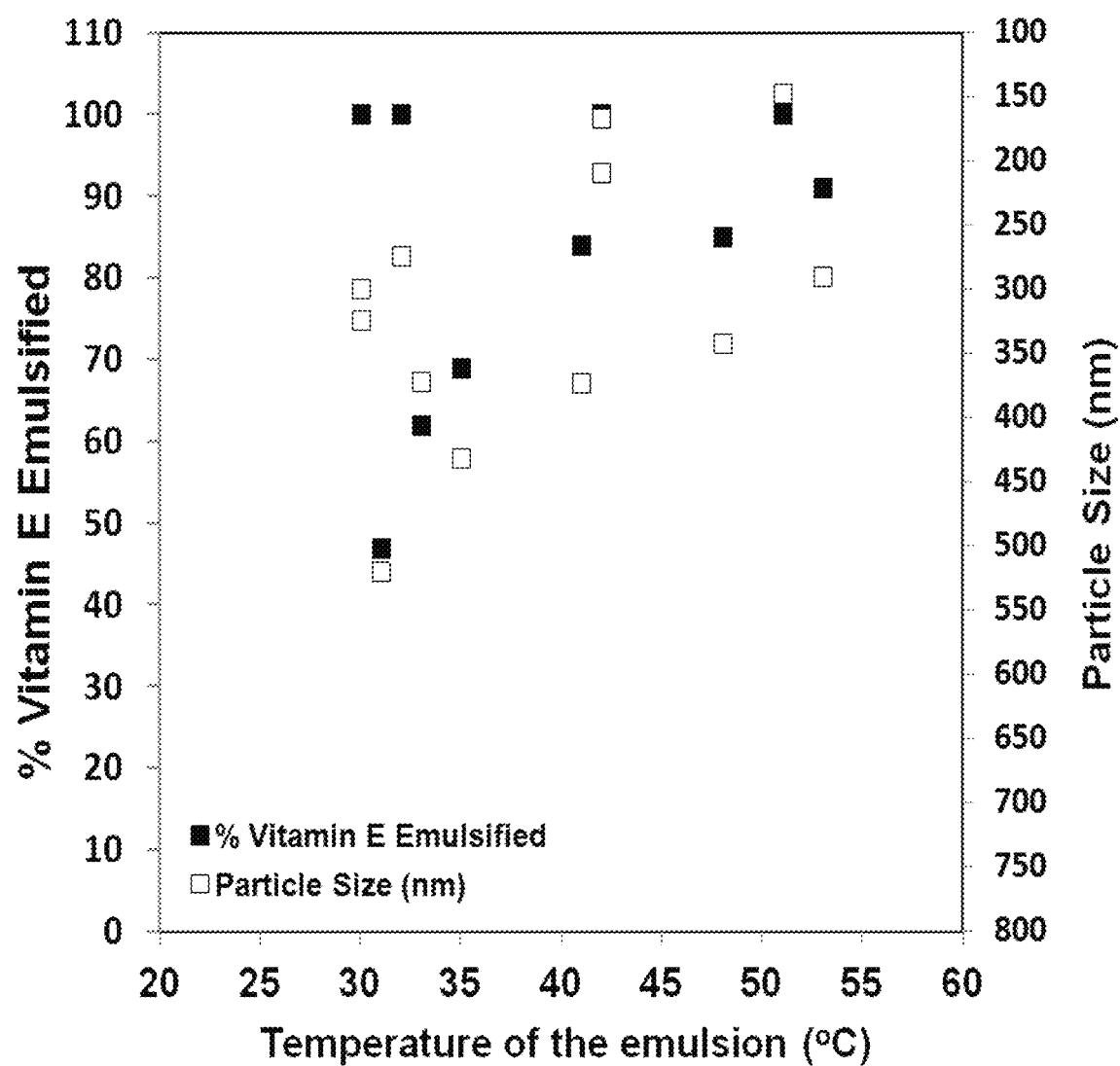
FIG. 17 is a plot of final emulsion temperature impacts on emulsion characteristics.

To investigate the effect of temperature, formulations were prepared at either low or high temperatures during the high shear homogenization step. For low temperature, the formulations were prepared at ambient conditions whereas for high temperature, formulations were prepared at 70° C. The results showed that temperature had no significant effect on the physical properties and stability of the emulsions. High temperature did not improve the properties of the emulsion. Therefore, it was concluded that emulsions could be readily prepared at room temperature. Instead, a more critical parameter may be the operational temperature at the end of the high-pressure homogenization step. Increasing pressure and number of cycles during homogenization was found to raise the temperature of the developed emulsion. The average temperature of the emulsions at exit ranged from 30° C. when the emulsions were prepared using 5 cycles at 5000 Psi to 53° C. for the emulsion made using 25 cycles at 25000 psi. Nonetheless, it could be readily seen that no correlation existed when the exit temperature from each run was plotted against measured particle size and the stability of the emulsions after 48 hours of storage. FIG. 17 shows the observed particle size (nm) and stability of the emulsions for each of the 12 Plackett-Burman runs as a function of the measured temperature of the same emulsions at the end of the high pressure homogenizing cycles. Stable submicron emulsions were successfully prepared at low temperatures. This may indicate that temperature has little or no effect on the quality of vitamin E/MCT emulsions when prepared using the parameters outlined in this study.

Parenteral lipid emulsions could be readily prepared by the high shear homogenization process. Preparing emulsions for highly viscous or polar oils, such as the case with vitamin E, is challenging. There is a need for emulsions with high vitamin E loading to serve as versatile carriers for co-administered drugs. Challenges associated with emulsifying vitamin E may be addressed by emulsifying blends of viscous vitamin E with low viscosity oil, such as MCT. This may also help lower the polarity of the oil phase and thereby increasing the ratio of emulsifiers at the oil/water interface. The present example confirmed this approach demonstrating the importance of the ratio of vitamin E to MCT on the quality and stability of the emulsions. Increasing the concentration of phospholipids or adjusting homogenization temperature did not improve the quality of the emulsions. Homogenization pressure and number of homogenization cycles was also shown to improve the quality of the emulsions. Overall, stable submicron emulsions with high vitamin E loading could be prepared at ambient temperature using 1.2% phospholipids and 0.5% Tween 80 (0.5%) at low vitamin E to MCT ratios.

Materials

Materials used in association with Examples 11-19 are were as follows. Vitamin E [(±)-α-Tocopherol] was purchased from Sigma (St. Louis, Mo.). polyoxyethylene sorbitan 20 monooleate sold as Tween® 80 and is referred to herein as Tween 80 and polysorbate 80 was provided by Uniqema (New Castle, Del.). Soybean Phospholipids containing a minimum of 80% phosphatidylcholine and 7-9.5% phosphatidylethanolamine sold as Lipoid E80S and referred to herein as Lipoid E80S or Lipoid was provided by Lipoid GmbH (Ludwigshafen, Germany). Caprylic/Capric triglyceride a medium-chain triglyceride sold as Miglyol® 812 referred to herein as MCT or Miglyol was provided by Sasol of Witten/Ruhr, Germany. Glycerol was purchased from Gallipot, Inc. (Saint Paul, Minn.). Poloxamer sold as 188 Lutrol® F 68 NF and referred to herein as Lutrol or poloxamer was obtained from BASF (Florham Park, N.J.). Sodium Deoxycholate was obtained from Alfa Aesar (Ward Hill, Mass.). Sodium Oleate was purchased from TCI AMERICA (Portland, Oreg.). Hemoglobin reagent set was purchased from Teco Diagnostic (Anaheim, Calif.). Whole Rabbit Blood was obtained from Hemostat Laboratories (Dixon, Calif.). Sodium chloride solution (0.9%) was obtained from Hospria Inc. (Lake Forest, Ill.); 14.6% sodium chloride solution was obtained from LyphoMed, Inc. (Melrose Park, Ill.); and 10% calcium gluconate solution was obtained from American Regent, Inc. (Shirley, N.Y.). Human Plasma was kindly donated by LifeShare blood center (Monroe, La.). Cell culture media RPMI+GlutaMax™-I, Trypsin and Phosphate buffer saline (PBS) were purchased from Invitrogen (Carlsbad, Calif.). MCF-7 and SW-620 cell lines were obtained from ATCC™ (Manassas, Va.). Insulin was bought from Sigma Chemical Company (St. Louis, Mo.) and penicillin-streptomycin was obtained from Cellgro® (Manassas, Va.). Detergent reagent SDS was purchased from Trevigen Inc. (Gaithersburg, Md.), Culture flasks (BD®) and 96-well plates (BD®), fetal bovine serum (HyClone Inc) were purchased through VWR (Westchester, Pa.). CellTiter-Glo® Luminescent Cell Viability Assay kits were purchased from Promega (Madison, Wis.). Double distilled (DI) water was used for all preparations. All other chemicals were of reagent grade or higher and were used without further modification.

Example 11

Emulsion Preparation

Emulsions (20 mL) were prepared by first mixing vitamin E with MCT at 3:7, 1:1, or 7:3 ratios to form the oil phase. The primary emulsifiers [1.2% Lipoid E80S and 0.5% Tween 80] were dissolved in DI water to form the aqueous phase of the emulsion to which 2.25% glycerol was added to adjust tonicity. In the second step of the optimization process, co-emulsifiers (poloxamer 188, sodium oleate, and sodium deoxycholate) were added to the aqueous phase at a concentration ranging from 0.5 to 3.5% by weight of the final emulsion. The oil and the aqueous phases were then mixed at 15000 rpm for 2 minutes using an mixer produced by IKA Works Inc., NC, USA and sold as the IKA® Ultra-Turrax T8 to form the crude pre-emulsion. The final concentration of the oil phase in the emulsions was 10, 15 or 20% w/w based on the experimental design as given in Table 6 shown below. A submicron emulsion was obtained by passing the coarse pre-emulsion through a high-pressure homogenizer made by Avestin Inc, Ottawa, Canada and sold as the EmulsiFlex® C3 homogenizer for several cycles and under homogenization pressure predefined by the statistical design as shown in Table 6. The temperature of the resulting emulsions was measured and the pH was adjusted to 8±0.05 using 0.1 N sodium hydroxide solution. The osmolality of the emulsions was measured using an automatic high sensitivity osmometer available from Precision Systems Inc., Natick, Mass. and sold as the 5002 OSMETTE™. For sterilization tests, 2 mL of each emulsion was placed in a vial and sterilized by autoclaving at 121° C. for 15 minutes.

Example 12

Multi-Variable Test

Processing and composition variables of the primary emulsions were tested by response surface methodology (RSM). A 4-factor, 27-run, Box-Behnken design was used to study the effect of homogenization pressure, number of homogenization cycles/passes, % oil loading, and the ratio of vitamin E in the oil phase on emulsion stability. The independent variables in the present study were homogenization pressure ($X_1$), number of homogenization cycles/passes ($X_2$), % oil loading ($X_3$), and the ratio of vitamin E to MCT in the oil phase ($X_4$). The dependent variables were % vitamin E that remained emulsified after 7 days of storage at ambient conditions ($Y_1$) and particle size ($Y_2$).

Table 6 lists the factors and dependent responses of the Box-Behnken design. This table also shows the low, medium and high levels of each independent variable (factor). In ANOVA analysis, low levels are coded as −1, medium level as 0 while high levels are coded as 1.

TABLE 6

| | Low Level (−1) | Middle level (0) | High Level (1) |
|---|---|---|---|
| Independent factors | | | |
| $X_1$: Homogenization Pressure (psi) × 1000 | 5 | 15 | 25 |
| $X_2$: Number of Cycles | 5 | 15 | 25 |
| $X_3$: % Vitamin E in the Oil Phase (%) | 30 | 50 | 70 |
| $X_4$: % Oil Phase in the Emulsion (%) | 10 | 15 | 20 |
| Dependent factors (responses) | | | |
| $Y_1$: % Vitamin E remaining emulsified after 7 days of storage $Y_2$: Particle Size (nm) | | | |

Table 7 below shows the 27 runs of the Box-Behnken design. Also shown is the exact level of the independent variable used for each run and the observed responses at the conclusion of each experiment.

TABLE 7

| RUN | Factors (Independent Variable) | | | | Observed Responses | |
|---|---|---|---|---|---|---|
| | $X_1$ | $X_2$ | $X_3$ | $X_4$ | $Y_1$ | $Y_2$ |
| 1 | 15 | 25 | 30 | 15 | 98 | 213 |
| 2 | 15 | 15 | 50 | 15 | 94 | 247 |
| 3 | 25 | 15 | 50 | 20 | 95 | 260 |
| 4 | 15 | 25 | 50 | 20 | 100 | 250 |
| 5 | 15 | 5 | 50 | 20 | 68 | 354 |
| 6 | 5 | 15 | 30 | 15 | 90 | 261 |
| 7 | 15 | 25 | 50 | 10 | 94 | 246 |
| 8 | 25 | 25 | 50 | 15 | 93 | 255 |
| 9 | 25 | 5 | 50 | 15 | 63 | 304 |
| 10 | 15 | 5 | 70 | 15 | 24 | 424 |
| 11 | 25 | 15 | 70 | 15 | 67 | 350 |
| 12 | 15 | 25 | 70 | 15 | 33 | 348 |
| 13 | 5 | 25 | 50 | 15 | 44 | 372 |
| 14 | 15 | 5 | 30 | 15 | 76 | 249 |
| 15 | 25 | 15 | 50 | 10 | 88 | 237 |
| 16 | 5 | 15 | 50 | 20 | 28 | 431 |
| 17 | 15 | 15 | 30 | 10 | 87 | 288 |
| 18 | 5 | 15 | 70 | 15 | 17 | 633 |
| 19 | 15 | 15 | 70 | 10 | 46 | 405 |
| 20 | 25 | 15 | 30 | 15 | 96 | 234 |
| 21 | 5 | 15 | 50 | 10 | 56 | 346 |
| 22 | 15 | 15 | 50 | 15 | 90 | 310 |
| 23 | 15 | 5 | 50 | 10 | 54 | 344 |
| 24 | 15 | 15 | 30 | 20 | 90 | 284 |
| 25 | 5 | 5 | 50 | 15 | 29 | 541 |
| 26 | 15 | 15 | 50 | 15 | 91 | 317 |
| 27 | 15 | 15 | 70 | 20 | 68 | 479 |

Addition of MCT to vitamin E in the oil phase reduced the viscosity of the blend and provided a hydrophobic core to stabilize the oil/water interface. The MCT was important as vitamin E when used alone was found to form a paste or a crude dispersion during initial homogenization that would quickly phase separate due to its high viscosity. Vitamin E is more polar than MCT because of the hydroxyl group on the aromatic chromanol ring. Not wishing to be bound by theory the polarity may result in higher solubility of phospholipids in vitamin E, which consequently may lower the availability of emulsifier at the vitamin E/water interface.

In each run, the concentration of the primary emulsifiers, made from a blend of 1.2% phospholipids and 0.5% Tween 80 was kept constant. Data generated for each response were subsequently fitted into quadratic models. Analysis of variance (ANOVA) was carried out to identify the significance of each model and its ability to predict the response with minimal residuals.

Table 8 shows the analysis of variance (ANOVA) for the responses ($Y_1$ and $Y_2$) showing the F-Ratio and significance (p-Value) of each factor on the measured response.

TABLE 8

| Source | $df^a$ | $Y_1$ [% Vit. E remaining emulsified after 7 days of storage] | | | | $Y_2$ [Particle Size] | | | |
|---|---|---|---|---|---|---|---|---|---|
| | | $SOS^b$ | $MS^C$ | F-Ratio | p-Value | $SOS^b$ | $MS^C$ | F-Ratio | p-Value |
| $X_1$ | 1 | 4720 | 4720 | 33.45 | 0.0001 | 74261 | 74261 | 39.02 | 0.0000 |
| $X_2$ | 1 | 1825 | 1825 | 12.94 | 0.0037 | 23585 | 23585 | 12.39 | 0.0042 |
| $X_3$ | 1 | 6627 | 6627 | 46.96 | 0.0000 | 102675 | 102675 | 53.95 | 0.0000 |
| $X_4$ | 1 | 48 | 48 | 0.34 | 0.5705 | 3072 | 3072 | 1.61 | 0.228 |
| $X_1^2$ | 1 | 1526 | 1526 | 10.82 | 0.0065 | 10561 | 10561 | 5.55 | 0.0363 |
| $X_1X_2$ | 1 | 56 | 56 | 0.4 | 0.5396 | 3600 | 3600 | 1.89 | 0.1942 |
| $X_1X_3$ | 1 | 484 | 484 | 3.43 | 0.0888 | 16384 | 16384 | 8.61 | 0.0125 |
| $X_1X_4$ | 1 | 306 | 306 | 2.17 | 0.1664 | 961 | 961 | 0.5 | 0.4909 |
| $X_2^2$ | 1 | 1309 | 1309 | 9.28 | 0.0102 | 85 | 85 | 0.04 | 0.8359 |
| $X_2X_3$ | 1 | 42 | 42 | 0.3 | 0.5943 | 400 | 400 | 0.21 | 0.6548 |
| $X_2X_4$ | 1 | 16 | 16 | 0.11 | 0.7421 | 9 | 9 | 0.00 | 0.9463 |
| $X_3^2$ | 1 | 996 | 996 | 7.06 | 0.0209 | 7500 | 7500 | 3.94 | 0.0705 |
| $X_3X_4$ | 1 | 90 | 90 | 0.64 | 0.4394 | 1521 | 1521 | 0.8 | 0.3889 |
| $X_4^2$ | 1 | 62 | 62 | 0.44 | 0.5191 | 261 | 261 | 0.14 | 0.7174 |
| Total error | 12 | 1693 | 141 | | | 22839 | 1903 | | |
| Total* | 26 | 18461 | | | | 265388 | | | |

[a] Degrees of Freedom,
[b] Sum of Squares, and
[c] Mean Square
*Total corrected.

Figure 18A:
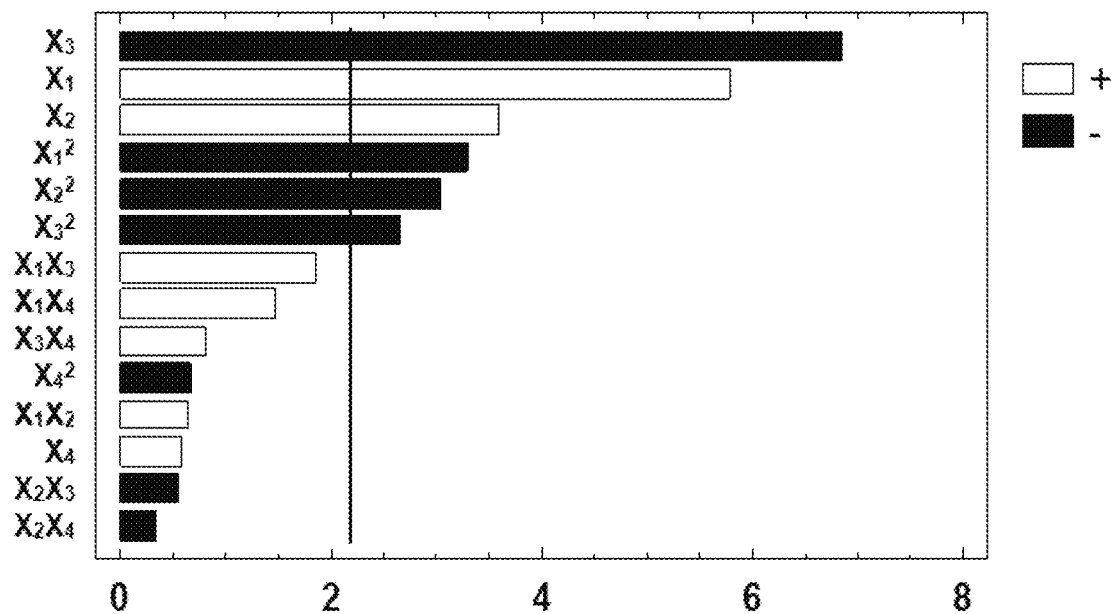
FIGS. 18A and 18B show the effects of variables on vitamin E emulsified after seven days of storage and particle size respectively.
Figure 18B:
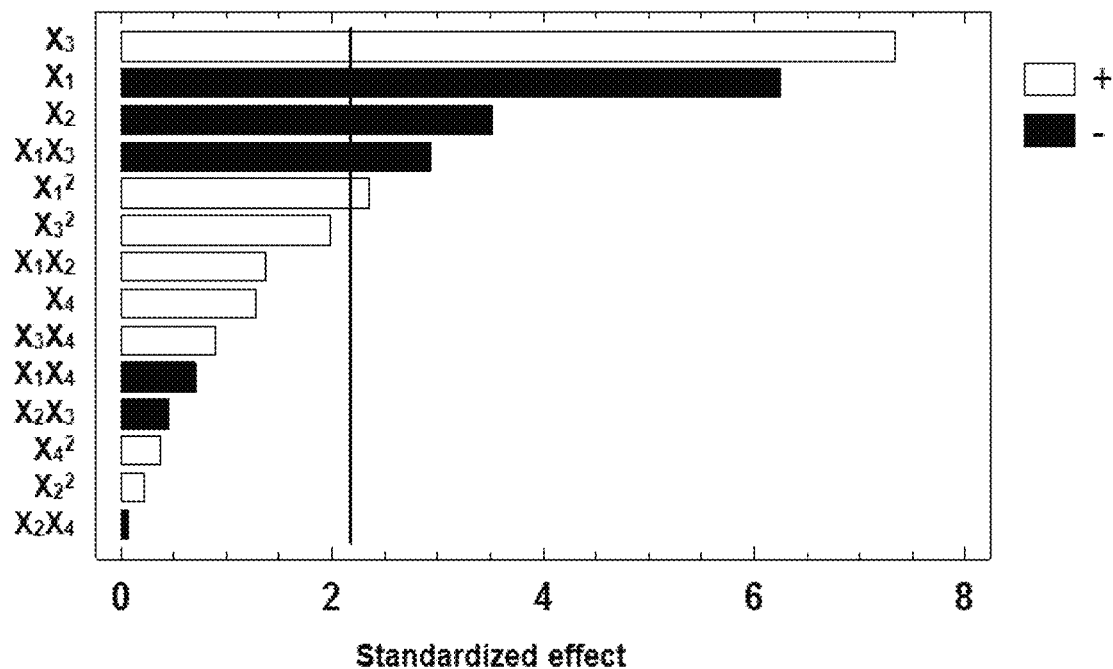

FIGS. 18A and 18B show Standardized Pareto charts showing the significance ($\alpha=0.05$) of each independent variable ($X_{1-4}$) and their quadratic and interaction effects on the responses (A) $Y_1$ [% Vitamin E that remained emulsified after 7 days of storage], (B) $Y_2$ [Particle Size]. White bars indicate a positive effect while black bars indicate a negative effect on the response. Bars that extend beyond the vertical line indicate a significant effect (p<0.05) of the factor on the response.

FIGS. 19A-19D show 3D response surface plots showing (A) the effect of homogenization pressure ($X_1$), and number of cycles ($X_2$) on the response $Y_1$ [% Vitamin E that remained emulsified after 7 days of storage], (B) the effect of homogenization pressure ($X_1$), and number of cycles ($X_2$) on the response $Y_2$ [particle size of the emulsions], (C) the effect of the percentage of vitamin E in the oil phase ($X_3$) and % of oil loading in the emulsion ($X_4$) on response $Y_1$, (D) the effect of the percentage of vitamin E in the oil phase ($X_3$) and % of oil loading in the emulsion ($X_4$) on response $Y_2$.

In the Box Behnken runs, the % vitamin E that remained emulsified varied from 17% (formulation 18) to 100% (formulation 4) while particle size varied from 213 nm (formulation 1) to 633 nm (formulation 18). Size and stability data were used to generate the following two polynomial equations, which were vital to understand the relationship between the independent and dependent variables:

$$Y_1 = 91.6667 + 19.8333X_1 + 12.3333X_2 - 23.5X_3 \pm 2.0X_4 - 16.9167X_1^2 + 3.75X_1X_2 + 11.0X_1X_3 + 8.75X_1X_4 - 15.6667X_2^2 - 3.25X_2X_3 - 2.0X_2X_4 - 13.6667X_3^2 + 4.75X_3X_4 - 3.41667X_4^2$$

Equation 1 (for the response $Y_1$):

$$Y_2 = 291.333 - 78.6667X_1 - 44.3333X_2 + 92.5X_3 + 16.0X_4 + 44.5X_1^2 + 30.0X_1X_2 - 64.0X_1X_3 - 15.5X_1X_4 + 4.0X_2^2 - 10.0X_2X_3 - 1.5*X_2X_4 + 37.5X_3^2 + 19.5X_3X_4 + 7.0X_4^2$$

Equation 2 (for the response $Y_2$):

In these equations, the magnitude and direction of the factor coefficient was used to explain the nature of factor effect [$X_1$-$X_4$] on the responses. Factors with coefficients of greater magnitude show a high effect on the response.

The regression coefficient obtained for both $Y_1$ and $Y_2$ was 91%, which indicates that the models as fitted explain 91% of the variability around the mean. By using ANOVA, it was also possible to calculate the significance of the ratio of mean square variation due to regression coefficient and residual error. Three factors [$X_1$, $X_2$ and $X_3$] had a significant effect on % vitamin E that remained emulsified after 7 days of storage (p<0.05), whereas [$X_4$] had no significant effect on this response. Similar analysis was carried out for the response $Y_2$ [Particle size]. For $Y_2$ however, only the quadratic effect of $X_1^2$ and the interaction effect $X_1X_3$ had a significant effect (p<0.05) on this response. For visual clarification, the significance of each independent variable on the responses was presented by Pareto Charts in FIGS. 18A and 18B.

The general conclusion of the above results was that high emulsification yield and low particle size could be attained by increasing homogenizing pressure and number of homogenization cycles and reducing the vitamin E to MCT ratio in the oil phase. The overall percentage of oil phase in the emulsion, however, had insignificant effect on emulsion stability within the tested range (10-20%), which was in contrast to the general observation that high oil concentrations often lead to remarkable increase in particle size as reported in previous studies. Increase in particle size is frequently attributed to the impoverishment of the surfactant at the interface with an increase in surface area of the dispersed oil phase. The insignificant effect of total oil load in this study, however, may be the result of the stabilizing effect of the excess phospholipids present in the emulsions. Using 1.2% phospholipid as a primary emulsifier is sufficient for the emulsification of vitamin E/MCT emulsions and increasing the concentration of phospholipids had no added advantage on the quality of the emulsions.

The percentage of vitamin E in the binary vitamin E/MCT blend of the oil phase, however, had a significant effect on the stability of the emulsions. Increasing the percentage of vitamin E in the blends from 30% to 70% was accompanied by a significant increase in particle size and creaming after seven days of storage. Aside from its polarity and its effect on the physico-chemical properties of the oil phase, the negative impact of high vitamin E to MCT ratio could also be attributed to the high viscosity of vitamin E. The viscosity of a 70% vitamin E blend was 460±5 mPa·s whereas the viscosity of the 30% vitamin E blend was 65±2 mPa·s.

Figure 19:
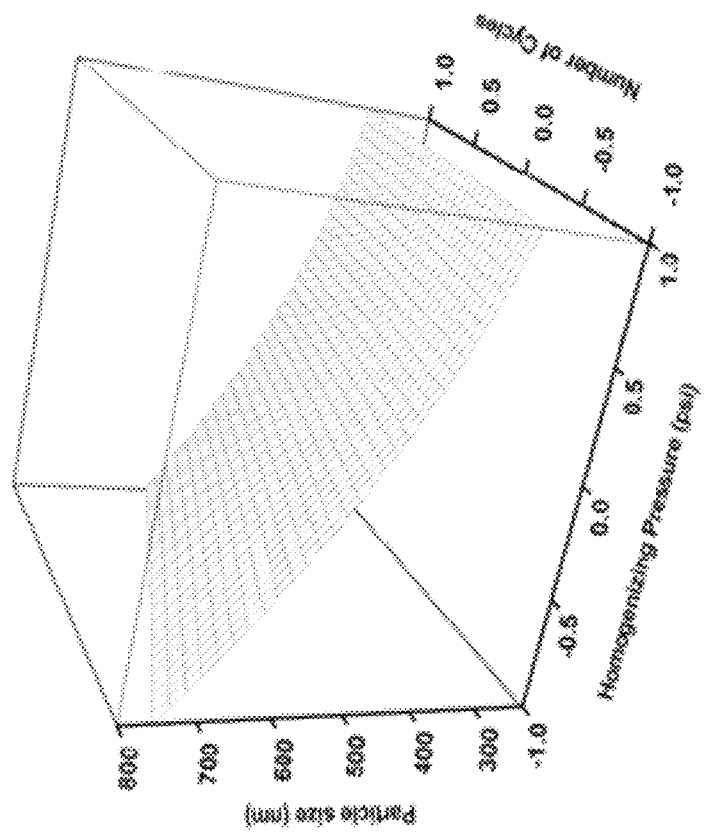
FIGS. 19A-19D plot the impact of multiple variables on vitamin E maintained in the emulsion and particle size.
Figure 19:
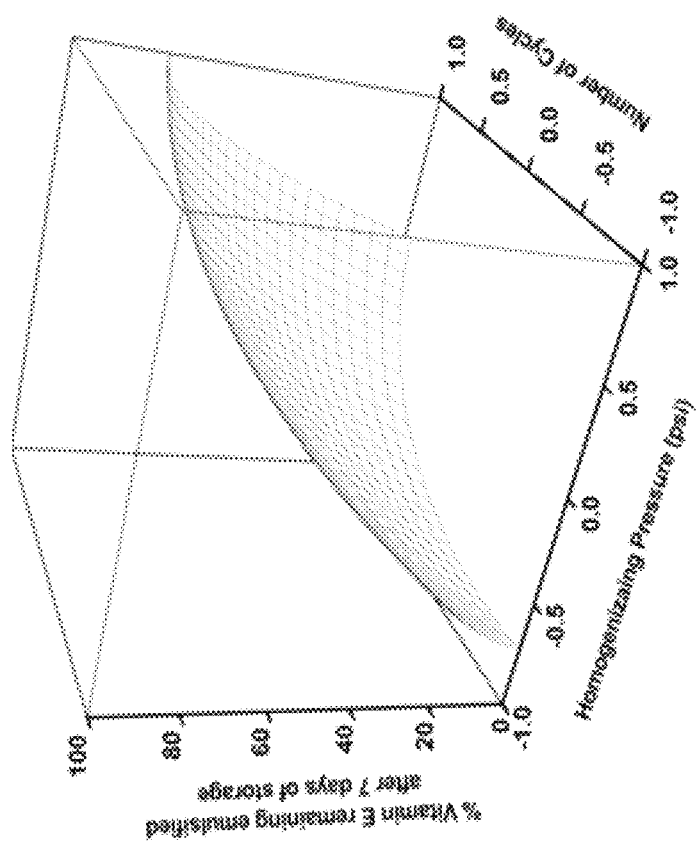
Figure 19:
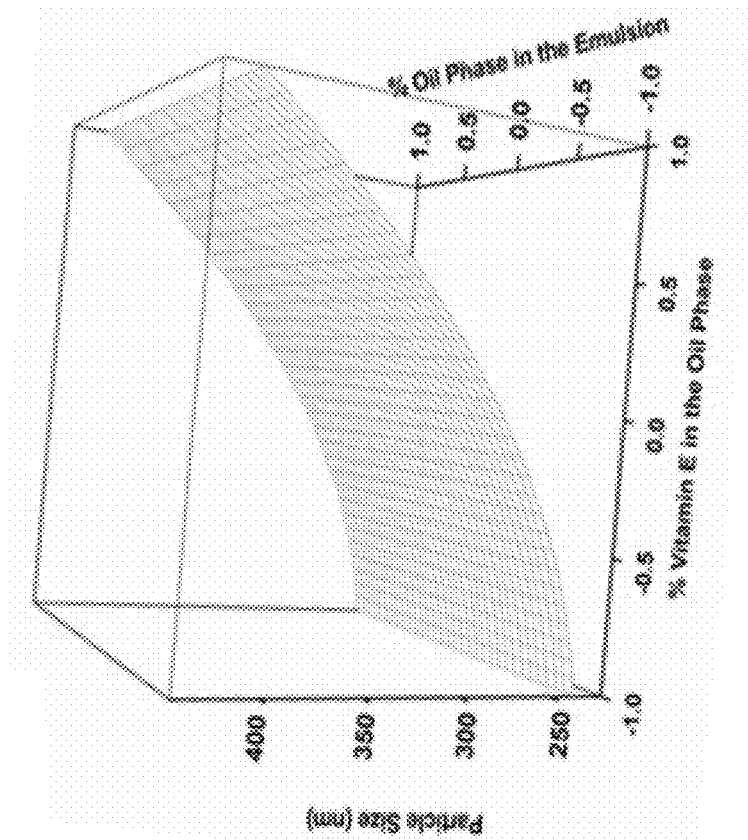
Figure 19:
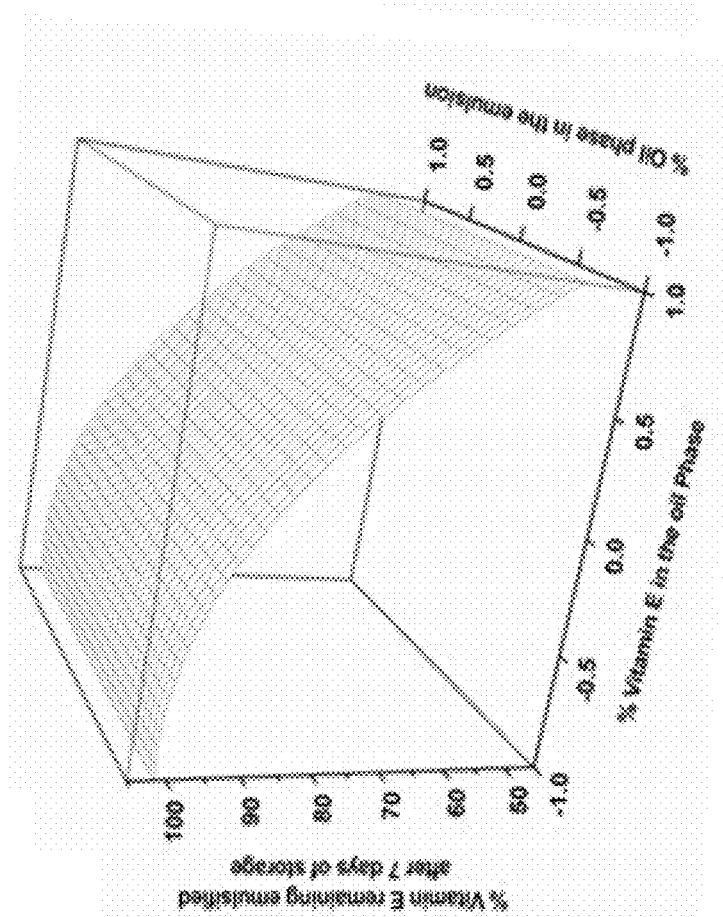

Dimensional response surface plots, as presented in FIGS. 19A-19D, are very useful to demonstrate the non-liner effects of factors on the responses. These plots show the effects of two factors on the response while maintaining the other two factors at mid level. For examples, the effect of $X_1$ and $X_2$ and their interaction on % vitamin E that remained emulsified after 7 days of storage [$Y_1$] at mid levels of $X_3$ and $X_4$ is given in FIG. 19A. As illustrated in this figure, when the pressure ($X_1$) increased from 5000 to 25000 psi and number of cycles increased from 5 to 25 passes, $Y_1$ increased non-linearly from 30% to 100%. Similarly, FIG. 19B shows the correlation between $X_1$ and $X_2$ and their effect on particle size ($Y_2$). The effects of $X_3$ and $X_4$ and their interaction on $Y_1$ and $Y_2$ are given in FIGS. 19C and 19D. As seen in the figures, $Y_1$ decreased with an increase in the concentration of Vitamin E in the binary vitamin E/MCT blend ($X_3$). On the other hand, particle size increased from 220 nm to 420 nm with a similar increase in the concentration of Vitamin E in the binary vitamin E/MCT blend. Oil loading ($X_4$), however, had insignificant effect on both responses as illustrated by the absence of any change in the response with a change in the magnitude of the factor.

Example 13

Secondary Emulsifier Test

From the Box Behnken study, it was concluded that the stability of vitamin E emulsions could be improved by increasing homogenization pressure and the number of cycles during the homogenization run. Increasing the load of vitamin E in the emulsions, however, had negative impact on their stability. Therefore, the ability of the secondary co-emulsifiers: sodium oleate, sodium deoxycholate, and polyoxyethylene-polyoxypropylene block copolymer (Poloxamer 188), to stabilize emulsions at a high vitamin E to MCT ratio was investigated. With poloxamers, the incorporation of the polyoxyethylene moieties may contribute to the steric stabilization of the emulsions, whereas sodium oleate and sodium deoxycholate may increase the negative charge potential of the emulsions and thereby contributing to their electrostatic repulsion. In this part of the study, secondary co-emulsifiers were used to prepare emulsions at 20% oil load with fixed vitamin E to MCT ratio of 7/3. Sodium oleate, sodium deoxycholate, and Poloxamer 188 were added at 0.5%, 1.5%, 2.5%, and 3.5% by weight of the total emulsion. A 3.5% Na Deoxycholate emulsion failed to form and therefore no results were reported for this formula. Initially, the mean droplet size of the emulsions was measured over 7 days of storage. On average, a droplet size of 5 μm is generally accepted as an upper limit. In the present study, vitamin E emulsions without secondary emulsifiers had an average droplet size of 350 nm. The addition of the secondary emulsifiers significantly decreased the droplet size to 200-250 nm, which was smaller than the average droplet size of commercial Intralipid® emulsion (about 300 nm), which was confirmed by STEM analysis as shown in the representative micrograph of poloxamer-stabilized emulsion given in FIG. 20B. No significant change was observed in droplet size on the emulsions after one months of storage at ambient conditions. The percentage of vitamin E that remained emulsified over the same period of time was also measured and the results are given in FIG. 20A. With the exception of Na deoxycholate emulsions, no decrease in the % vitamin E emulsified was observed when secondary co-emulsifiers were used.

Figure 20A:
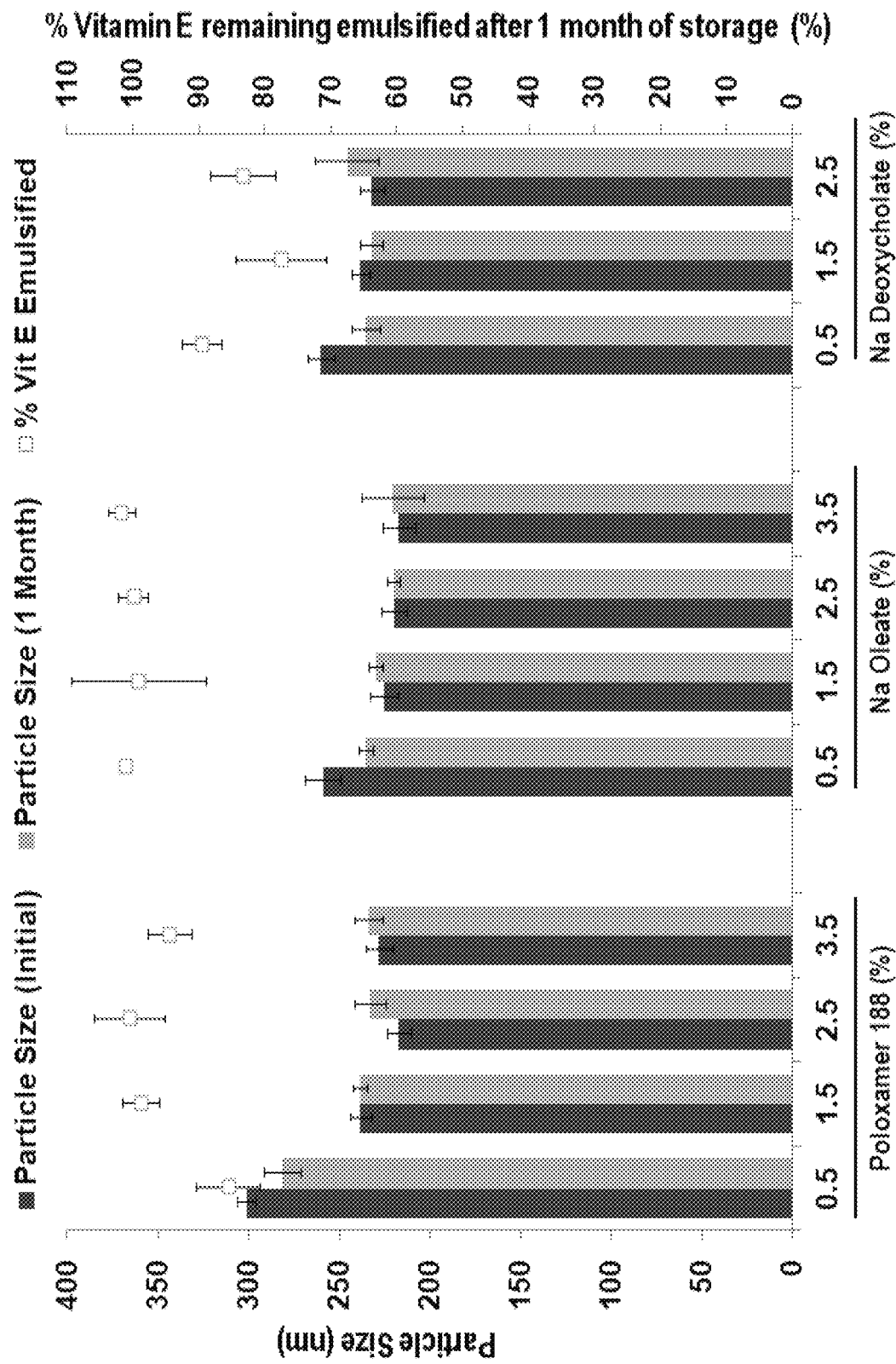
FIG. 20A is a graph of the effects of secondary emulsifiers on emulsion properties.
Figure 20:
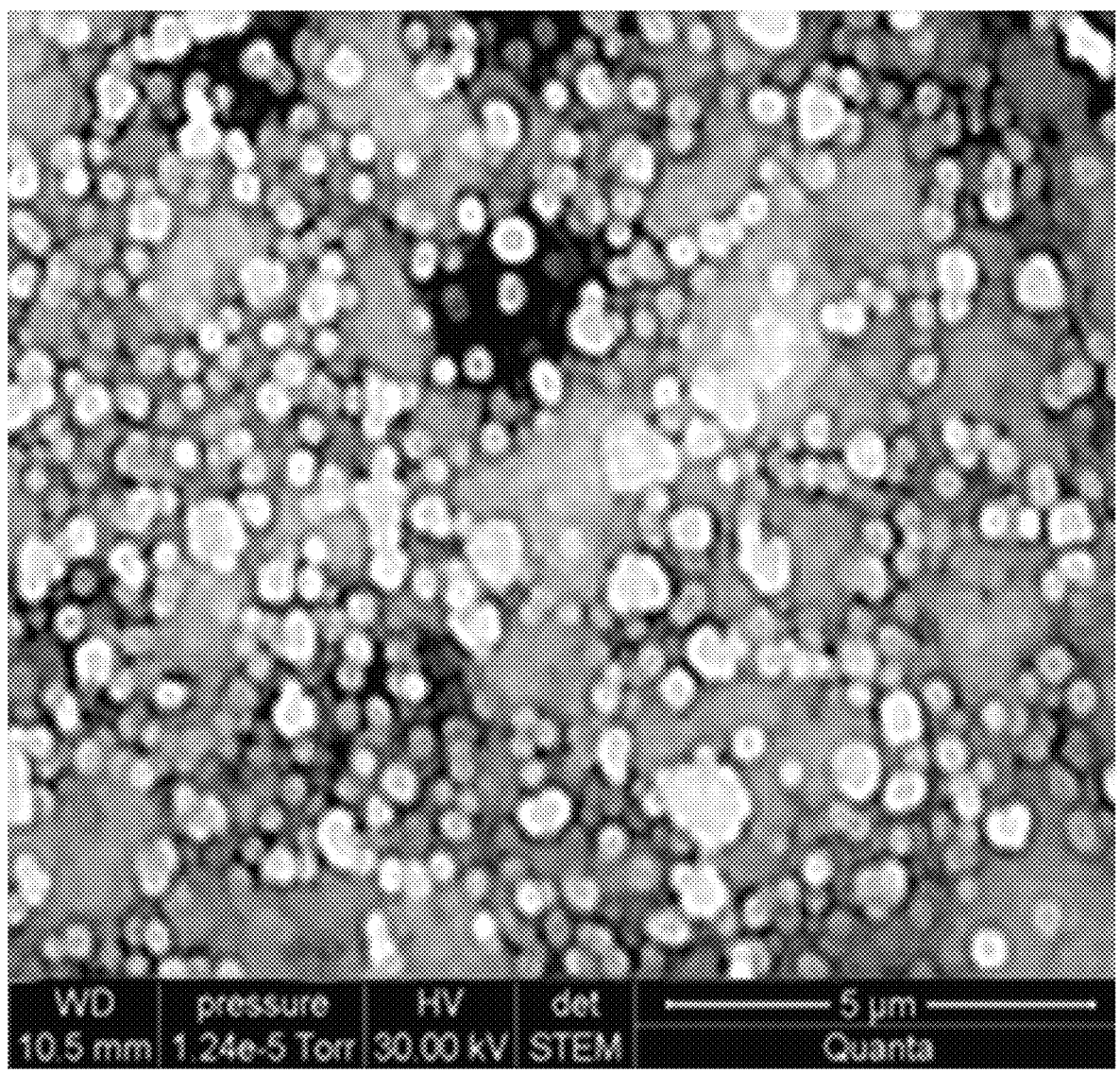
FIG. 20B is a scanning transmission electron photomicrograph of an emulsion.

FIG. 20A shows the particle size (left panel) and % vitamin E remaining emulsified after 1 month of storage (right panel) for three sets of vitamin E emulsions stabilized with 0.5-3.5% of secondary emulsifier (Poloxamer 188, Na Oleate, or Na Deoxycholate). No data were reported for emulsions stabilized with 3.5% Na Deoxycholate due to phase separation. Black bars and grey bars represent mean particle diameter ±SD at time zero and after 1 month of storage, respectively. Open boxes represent the % vitamin E remaining emulsified after the one month of storage.

Example 14

Emulsion Characterization

Sample characterization associated with Examples 11-19 was carried out as follows. Intensity-weighed mean particle size and population distribution (polydispersity index) of the emulsions were measured by photon correlation spectroscopy (PCS) at 23° C. and a fixed angle of 90° using Nicomp™ 380 ZLS submicron particle size analyzer (PSS Inc., Santa Barbara, Calif.). Emulsions were diluted with DI water in order to avoid multiple scattering and to achieve the scattering intensity of 300 kHz. The intensity-weighted mean diameter of the particles was calculated based on Stokes-Einstein law by curve fitting of the correlation function. Zeta-potential of the SLN was measured using the same instrument (Nicomp™ 380 ZLS) under zeta mode. Samples were diluted with DI water and zeta-potential was measured using the Helmholz-Smoluchowsky equation. Short-term stability was assessed by measuring the size and concentration of vitamin E remaining emulsified after storage at ambient conditions for 7 days. The percentage of vitamin E emulsified was determined by first removing any separated oils from the surface of the emulsion. The content of vitamin E remaining emulsified was then determined by analyzing a sample (0.1 mL) collected from the bulk of the emulsion spectrophotometrically at 295 nm (Cary 50 probe-UV spectrophotometer, Varian Inc., Cary, N.C.). Before analysis, each sample was diluted to 4 mL with methanol. From this stock, 0.1 mL was further diluted to 2 mL with methanol. UV calibration curve was developed from a methanolic TRF solution. No spectral overlaps or interferences from lipids and other constituents of the emulsion were observed.

Example 15

Microscopy

STEM was used to determine the morphology of the vitamin E lipid emulsion. The emulsion was diluted 500 fold with distilled water and was negatively stained with 10% phosphotungstic acid for contrast enhancement. Staining was allowed to proceed for few minutes in air at room temperature. A small drop was spread onto a Formvar® coated STEM copper grid (400 mesh), and the excess liquid was removed with kimwipe tissue paper. The grid containing the emulsion was observed at ~$5\times10^{-6}$ torr vacuum and 30 keV beam energy with a Type FP 2012/13 quanta 200 electron microscope (FEI, Hillsboro, Oreg.). Particle sizing was accomplished via image processing with ImageJ Version 1.46 m provided by the National Institutes of Health. The image was threshold processed and converted into binary form for particle sizing via particle area selection and inclusion. FIG. 20B shows Scanning transmission electron photomicrograph (STEM) of the 2.5% Poloxamer-stabilized TRF lipid emulsion.

Example 16

Stress Tests

Emulsions were subjected to a mechanical shaking test. Samples were placed randomly on a shaker (Barnstead International, Dubuque, Iowa) and agitated at the maximum amplitude of 250 strokes/min for 24 hours at room temperature. At the end of each test, samples were visually inspected for signs of phase separation and then analyzed for size.

Figure 21:
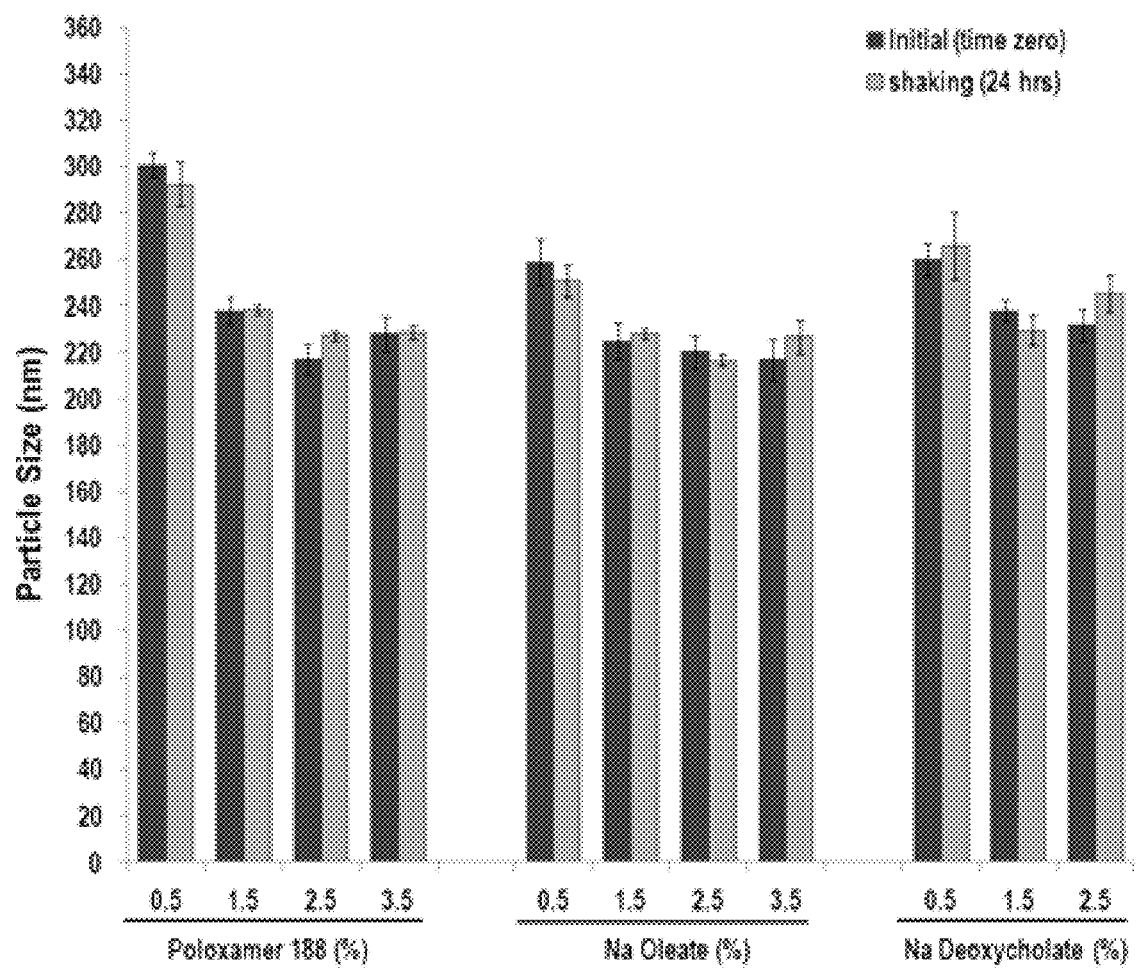
FIG. 21 is a plot of the particle size of various emulsions after shaking.

To access the physical stability of these emulsions and to estimate their destabilization processes, the change in the average droplet size of the emulsions under different stress conditions was measured. For an initial test, no significant change in droplet size was observed after shaking the emulsions for 24 hours. See FIG. 21. On visual inspection, all formulations were homogenous and no visible free oil or breakage of the systems was seen.

Figure 22:
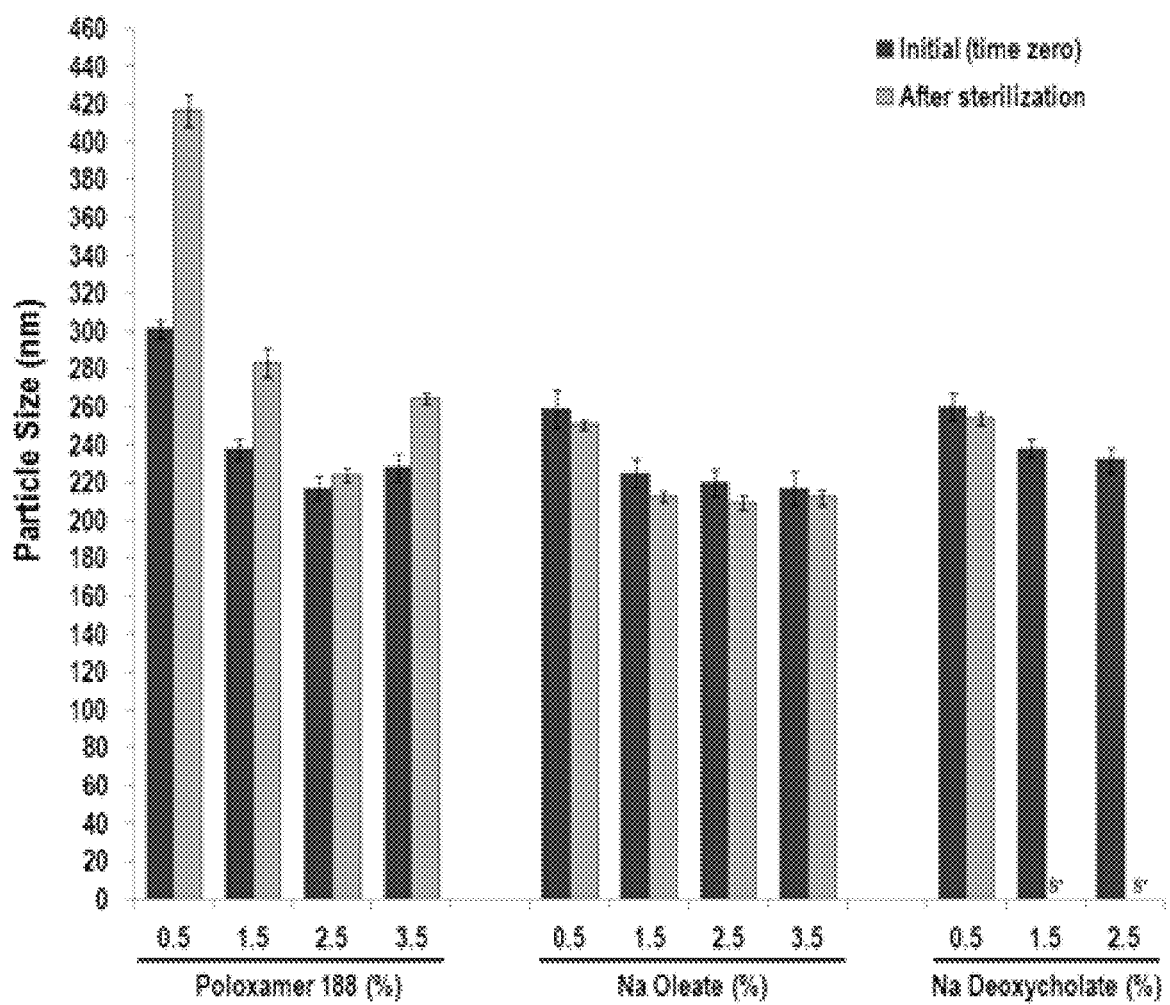
FIG. 22 is a plot of the particle size of various emulsions after heat treatment.

Since lipid emulsions are thermodynamically unstable, vitamin E emulsions were autoclaved to accelerate their degradation. Data generated from the sterilization study were then used as an alternate accelerated stability test. Similar to shaking test, most of the emulsions exhibited good stability except for those stabilized with Na deoxycholate and poloxamer at low concentrations, which exhibited a significant increase in droplet size as a result of energy induced coalescence or complete phase separation. Results from the heat degradation tests are shown in FIG. 22.

Example 17

Stability Tests

An aliquot (0.05 mL) of each emulsion was mixed with 0.5 mL of human plasma or an electrolyte solution. Samples were then incubated while rotating at 37° C. in a gravity convection oven (Model: 1350GM, Sheldon Manufacturing Inc, Cornelius, Oreg.) for 24 h. The electrolyte solutions were 10% calcium gluconate (0.465 mEq/mL), 0.9% NaCl (0.154 mEq/mL) and 14.6% NaCl (2.5 mEq/mL) solutions. At the end of the experiments, samples were visually inspected and then analyzed for particle size. Zeta potential was measured and compared with those of the emulsions before they were mixed with plasma or electrolyte solutions.

Figure 23:
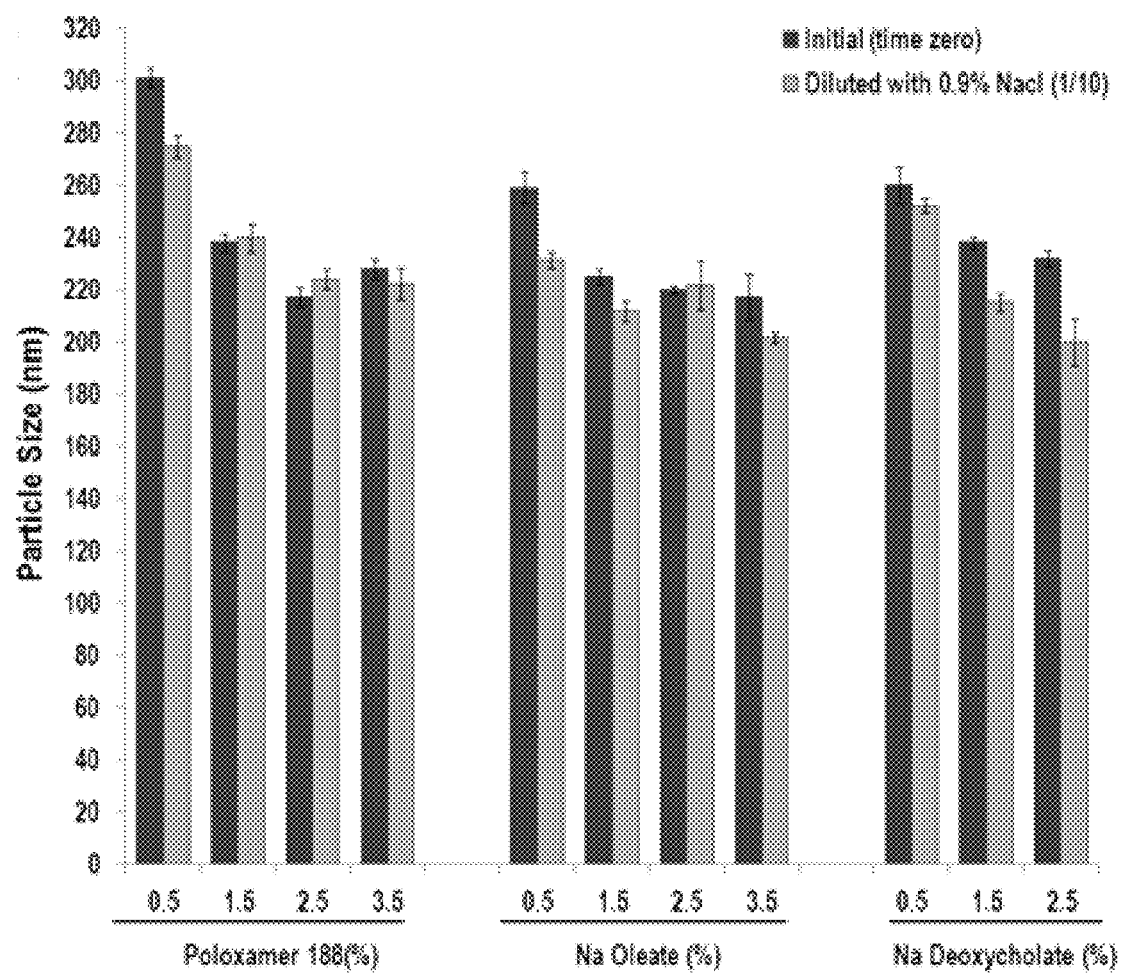
FIG. 23 is a plot of the particle size of various emulsions after treatment with a solution of NaCl.
Figure 24:
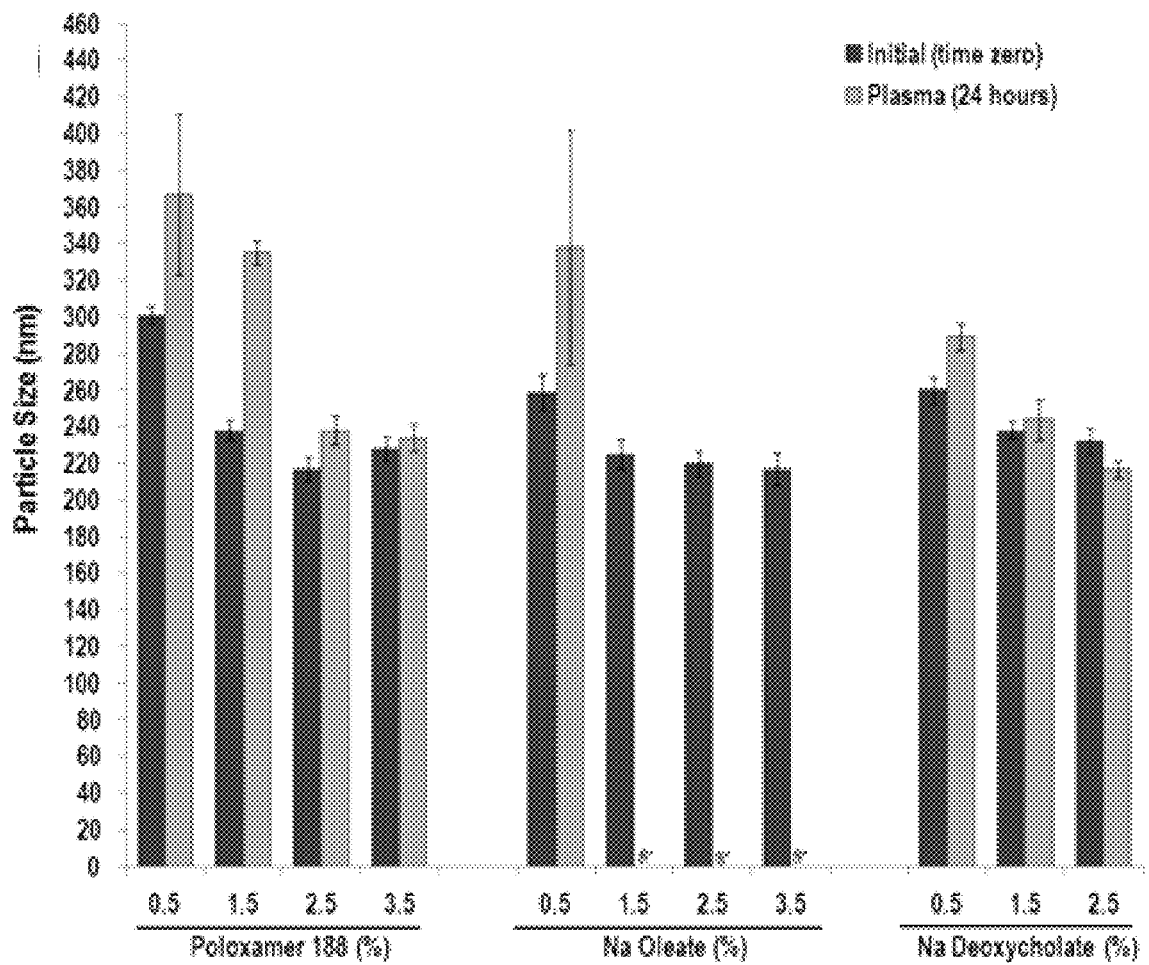
FIG. 24 is a plot of the particles size of various emotions after treatment with plasma.

FIGS. 23 and 24 show the effect of NaCl and plasma respectively on stability of vitamin E emulsions fortified with up to 3.5% of secondary emulsifiers. Collectively FIGS. 21-24 show the effects of (A) shaking for 24 hrs on particle size; (B) sterilization at 121° C. for 15 minutes on particle size; (C) 1:10 dilution with 0.9% NaCl on particle size after 24 hours of storage; and (D) 1:10 dilution with plasma at 37° C. under rotation for 24 hrs on particle size.

In this study, the nonspecific adsorption of the monovalent cation ($Na^+$) on the surface of the emulsions at low concentration (0.9% NaCl containing 154 mEq/L sodium and 154 mEq/L chloride) had insignificant effect on droplet size. However, when the concentration of $Na^+$ was increased to 2500 mEq/L (14.6% NaCl), the zeta potential significantly fell to the point where emulsions were unable to overcome the attractive Van der Waals force. At this point, the force became predominantly attractive resulting in emulsion flocculation. This phenomenon was observed with emulsions stabilized with Na oleate and Na deoxycholate.

FIGS. 25A-25D show the effect of highly concentrated mono and divalent electrolyte solutions on the stability of three sets of vitamin E emulsions fortified with up to 3.5% of secondary emulsifiers after 24 hours of storage. This figure shows the change in droplet size after 1:10 dilution with (A) 14.6% NaCl solution and (B) 10% calcium gluconate solution. Also shown is the corresponding change in zeta potential after 1:10 dilution with (C) 14.6% NaCl solution and (D) 10% calcium gluconate solution. Black and grey bars represent mean globule diameter and zeta potential +/−SD at initial time-point and 24 hours after dilution, respectively. Empty areas (without bars) with S letter represent the emulsions that underwent phase separation.

Figure 25:
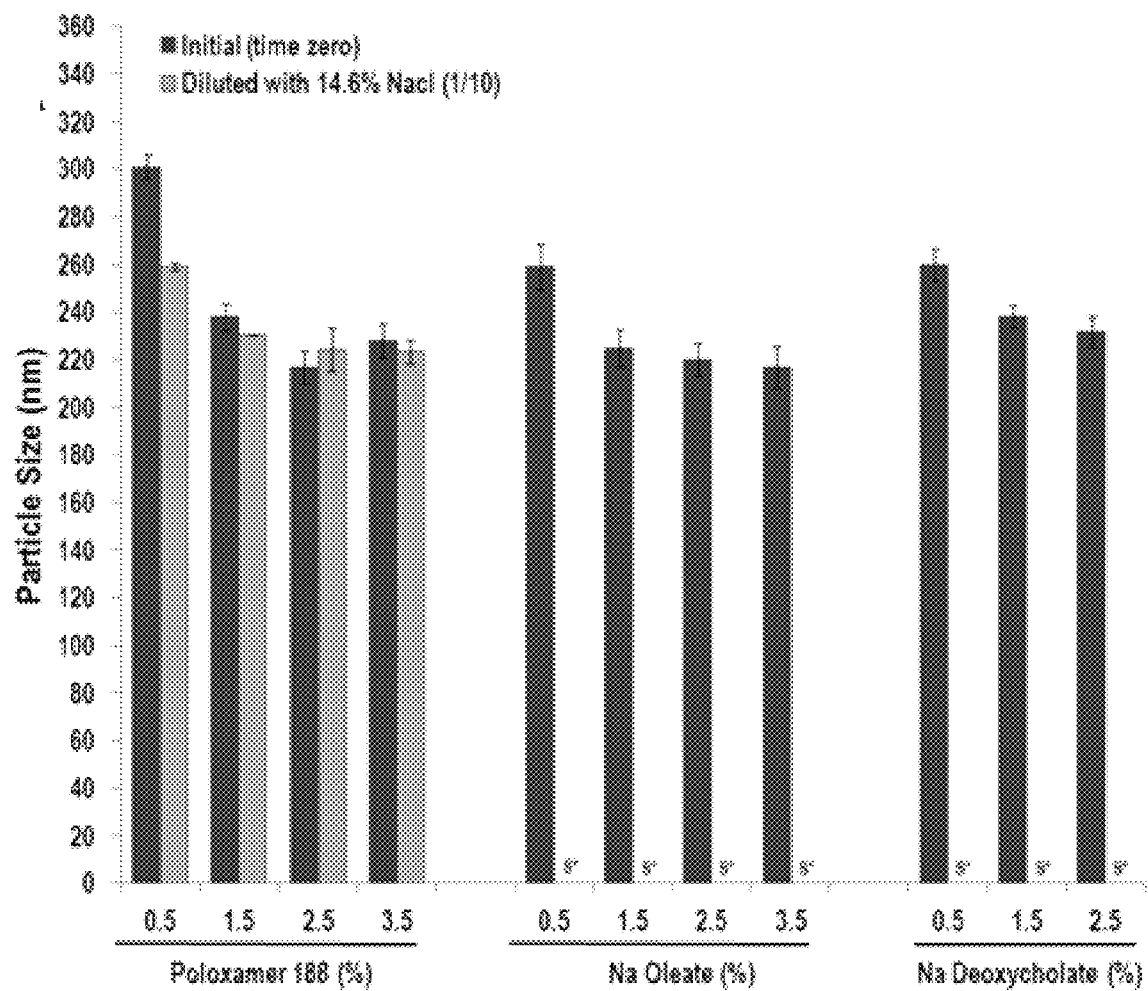
FIG. 25A is a plot of the particle size of various emulsions after treatment with a solution of NaCl.
FIG. 25B is a plot of the particle size of various emulsions after treatment with calcium gluconate.
FIG. 25C is a plot of Zeta potential of various emulsions after treatment with a solution of NaCl.
FIG. 25D is a plot of Zeta potential of various emulsions after treatment with calcium gluconate.
Figure 25:
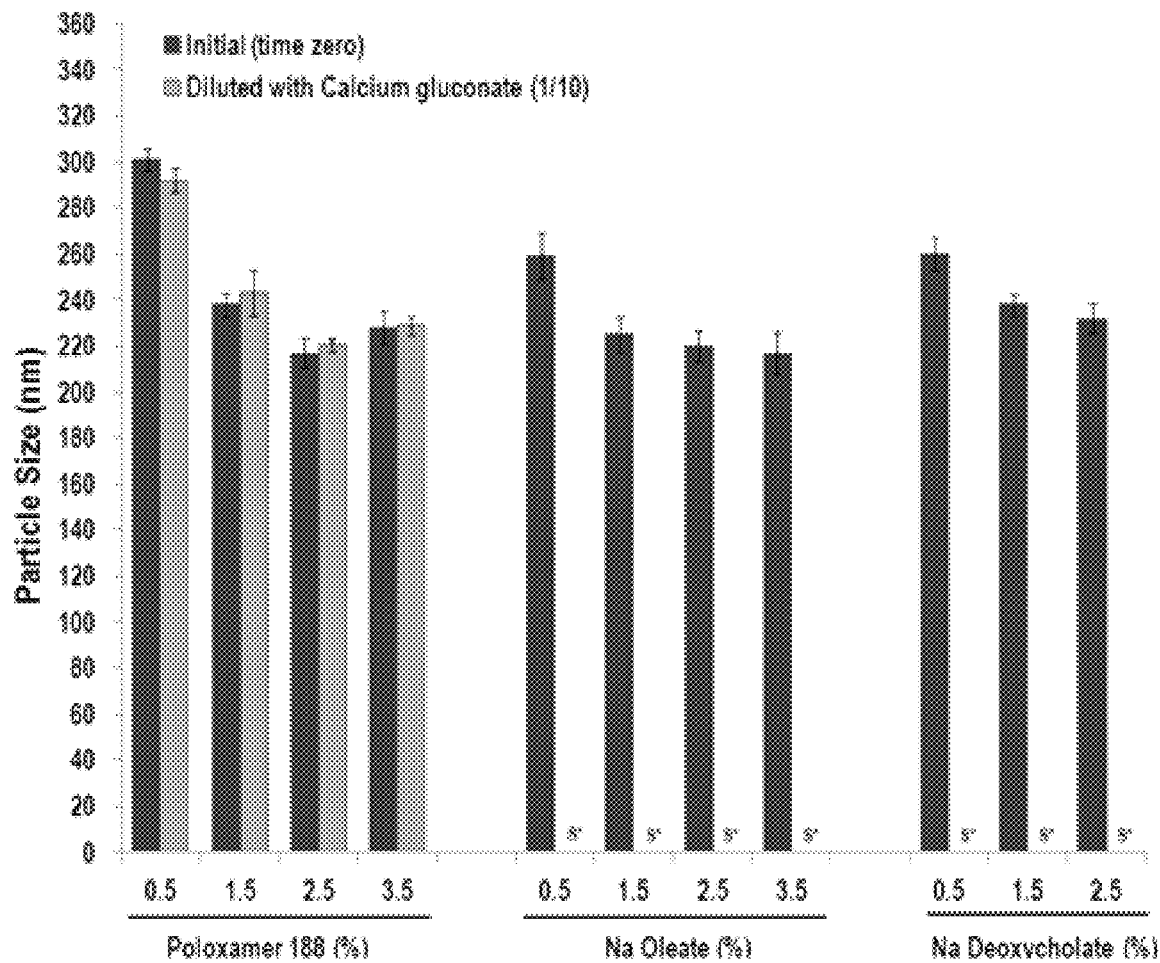
Figure 25:
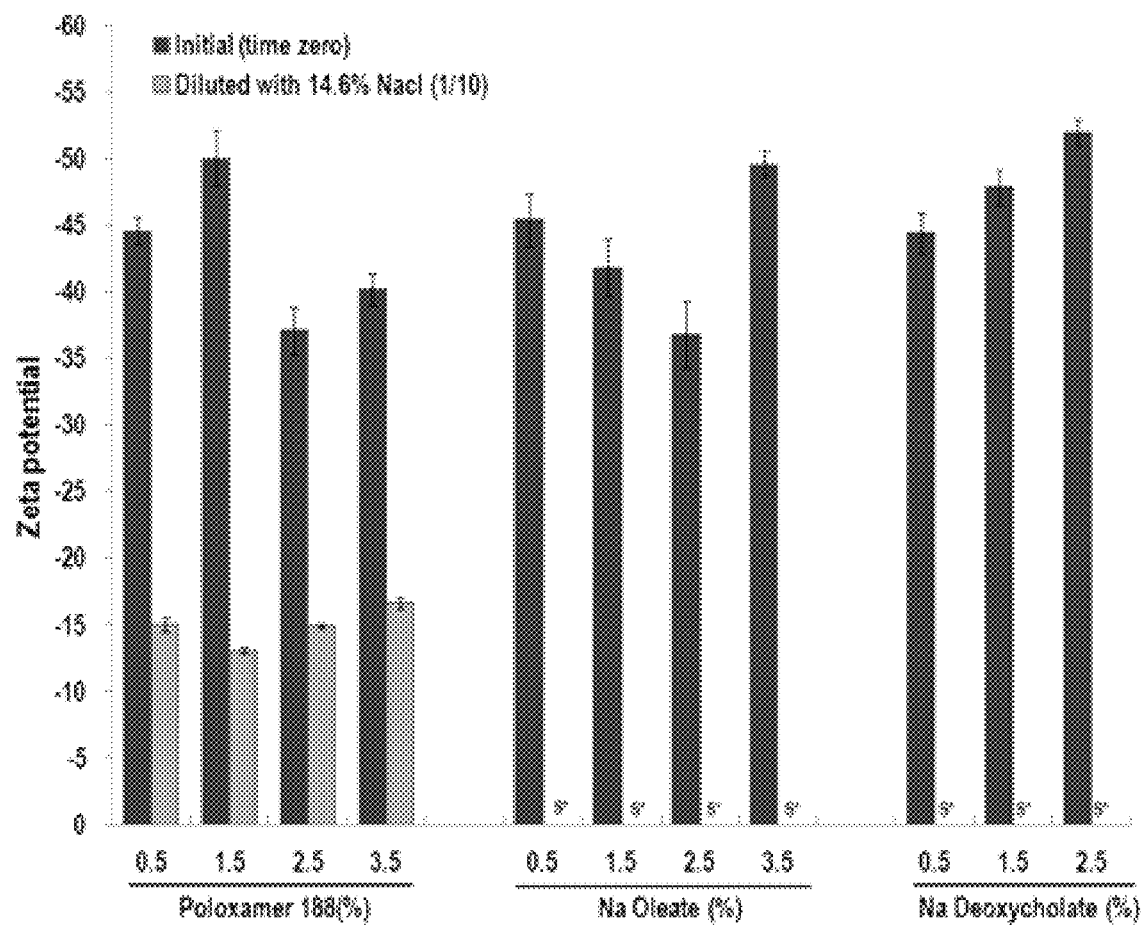
Figure 25:
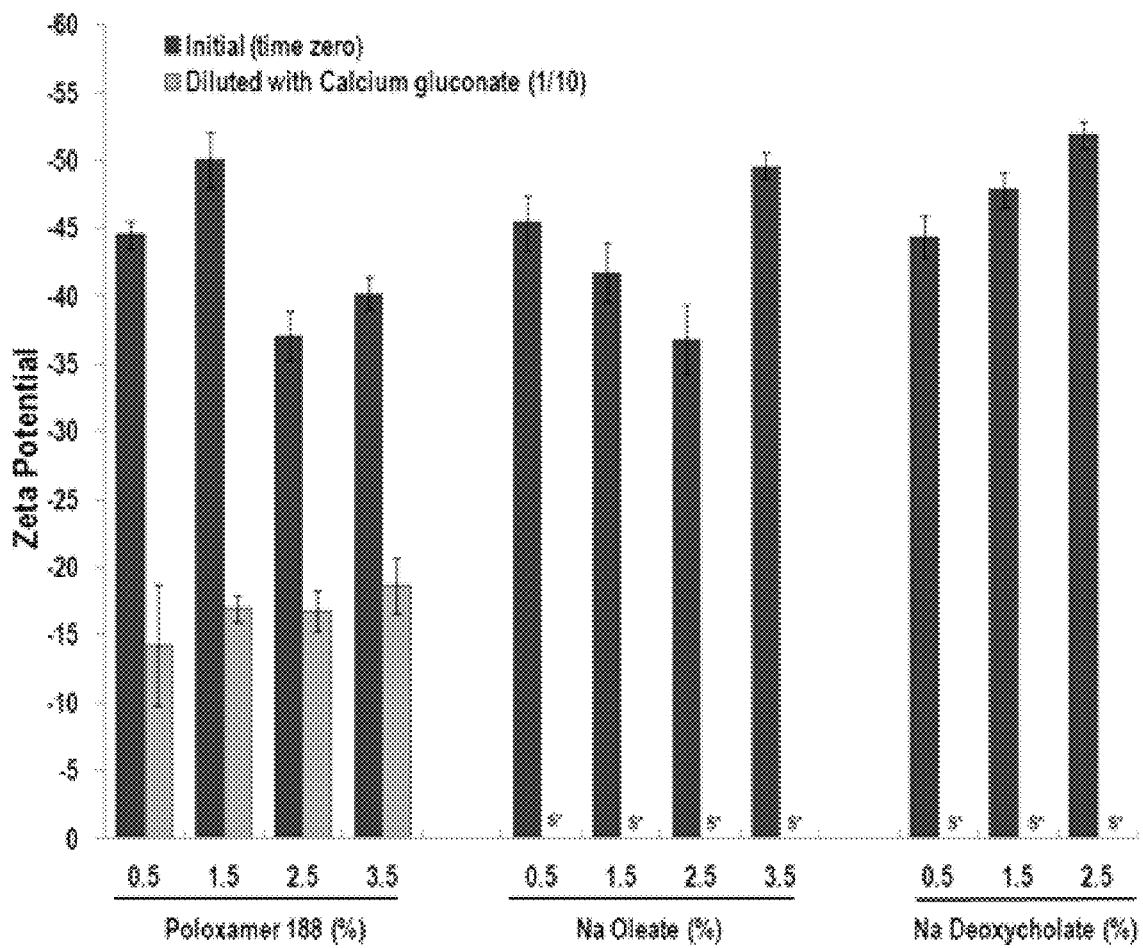

The initial zeta potential of the emulsions was approximately −40 to −50 mV, which significantly dropped after the addition of NaCl (FIG. 25C). The negative zeta potential of the emulsions is attributed to the anionic fractions, mainly phosphatidylcholine, which was neutralized by the addition of the counterion. The stability of the poloxamer emulsions, however, may be attributed to the localization of their polyoxyethylene chains at the oil/water interface near the aqueous phase and thereby shielding the negative surface charge provided by the phospholipids. Similar results were observed when emulsions were diluted with a high concentration of the multivalent $Ca^{+2}$ ions (FIG. 25B). The Specific adsorption of $Ca^{+2}$ ions on phospholipid surfaces may have resulted in the flocculation and/or complete phase separation of emulsions stabilized with Na oleate and Na deoxycholate, which may be attributed to the reduction in zeta potential as discussed above and shown in FIG. 25D.

Since vitamin E emulsions are intended for subsequent use in animal models and clinical studies, their ex vivo stability in human plasma and their hemolytic effect on RBC were investigated. A significant increase in droplet size induced by droplet coalescence or complete phase separation was observed with emulsions stabilized with Na oleate or low concentrations of poloxamer. Only emulsions stabilized with sodium deoxycholate and high concentrations of poloxamer remained stable after 24 hours of incubation with plasma. Not wishing to be bound by theory, increased stability with increase in poloxamer concentration may be a result of the steric barrier formed by the bulky polyoxyethylene chains preventing the adsorption of proteins.

Example 18

Hemolysis

Hemolysis studies were performed as follows. Red blood cells were obtained by first centrifuging rabbit blood with normal blood chemistry at 800 g for 5 minutes to remove debris and serum proteins. The supernatant was discarded and the erythrocytes were re-suspended in isotonic phosphate buffer (pH 7.4). The washing step, which involved centrifugation and re-suspension in phosphate buffer, was repeated several times until an almost clear supernatant was obtained. Collected erythrocytes were then used to prepare a stock dispersion in DPBS/modified buffer with a fixed hemoglobin concentration of 8 g/dl. The stock dispersion was stored in a refrigerator for a maximum of 24 hours. The stability of the stock dispersion and the concentration of hemoglobin were checked by measuring absorbance at 540 nm. For hemolysis testing, 100 µL aliquot of each emulsion was first diluted with 0.8 mL of DPBS/modified buffer to which 100 µL of the stock erythrocyte dispersion was added. Mixtures were incubation at 37° C. for up to 180 minutes. After 30 and 180 minutes, debris and intact erythrocytes were removed by centrifuging the mixtures at 750 g for 3 min. From the supernatant, 100 µL was removed and dissolved in 2 mL of an ethanol-HCL mixture [39 parts of 99% ethanol (v/v) and 1 part of 37% hydrochloric acid (w/v)]. The absorbance of the resulting solution at 398 nm against a blank sample was used to estimate % hemolysis. Erythrocyte dispersion in buffer was used as the negative control (0% hemolysis) whereas a 1% dispersion in Triton (100% hemolysis) was used as the positive control.

The hemolytic effect induced by emulsions was measured after 30 and 180 minutes.

Figure 30:
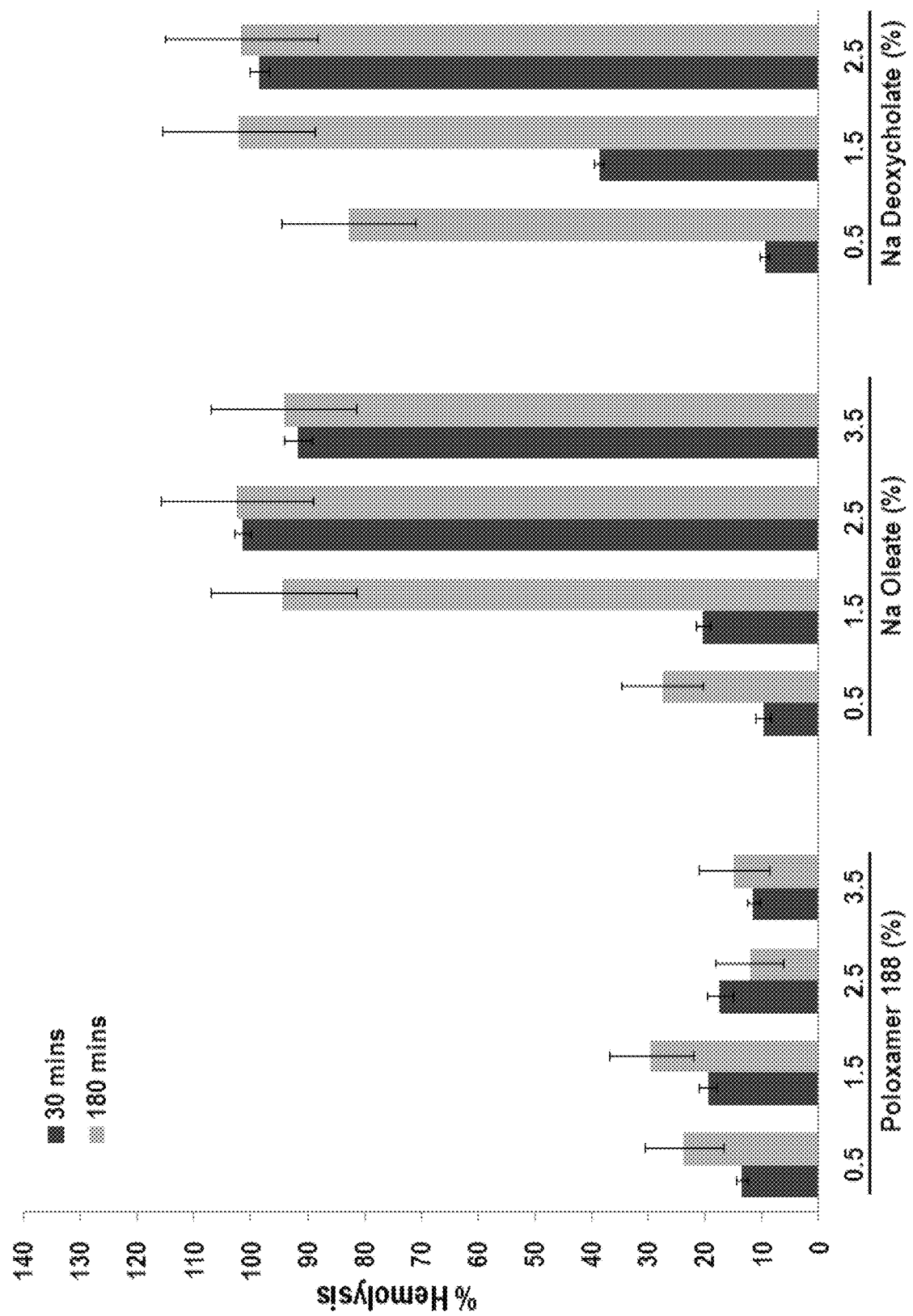
FIG. 30 is a plot of the hemolysis effects of various emulsions.

FIG. 30 shows the effect of type and concentration of secondary emulsifier used to stabilize the vitamin E emulsions on the hemolysis of rabbit blood after 30 and 180 minutes of incubation. Results are presented as mean±SD. All formulations induced hemolysis after 30 minutes, which significantly increased after 180 minutes, except for emulsions stabilized with high concentrations of poloxamer. This could be attributed to the ability of poloxamers to form an additional layer around the emulsifier mixed-film through its bulky polyoxyethylene head group, making it more difficult for emulsion particles to approach the erythrocytes. The significant increase in the hemolytic activity induced by Na oleate and Na deoxycholate reflects their toxic effect on erythrocytes.

Example 19

Antiproliferative Activity

The growth inhibitory activity of the TRF and tocopherol lipid emulsions against MCF-7 (human mammary adenocarcinoma) and SW-620 (human colon adenocarcinoma) cell lines was determined by using a luminescent cell viability assay sold as the CellTiter-Glo assay. MCF-7 and SW-620 cells were grown as monolayers in RPMI+GlutaMAX medium supplemented with 10% (v/v) fetal bovine serum, 1% (w/v) insulin and 1% (v/v) penicillin-streptomycin. Cells were cultured at 37° C. in a humid atmosphere of 5% $CO_2$. Once the cells reached confluence, $1 \times 10^4$ cells/well were seeded in a 96-well microtiter plate and incubated at 37° C. and 5% $CO_2$. After overnight incubation, cells were treated with 100 µL of TRF or tocopherol lipid emulsions, which were previously diluted with serum-free medium (SFM) to the desired concentration range (n=6). Treatments with lipid emulsions in fresh SFM were repeated every other day. Cells in SFM and cells treated with 0.1% SDS were examined in parallel as negative and positive controls, respectively. After 96 hrs of incubation, media were removed and 100 µL/well of CellTiter-Glo reagent diluted with phosphate buffer saline (PBS) was added. Plates were allowed to incubate at 37° C. for 10 minutes to stabilize luminescent signal, which was read by FLx800 fluorescence microplate reader (BioTek, Winooski, Vt.) The average luminescence reading obtained at each concentration was expressed as a percentage of the average luminescence readings obtained from control wells. Cell viabilities were calculated as percentage living cells. $IC_{50}$ values were determined from the logarithmic plots of the % viability versus concentration using statistical software.

No significant inhibition in cell viability was observed when cells were treated with tocopherol lipid emulsions within the concentrations that were evaluated in this study. Approximately 80% of MCF-7 cells and 100% of SW-620 cells remained viable when treated with tocopherol at concentrations as high as 25 µM.

Figure 31:
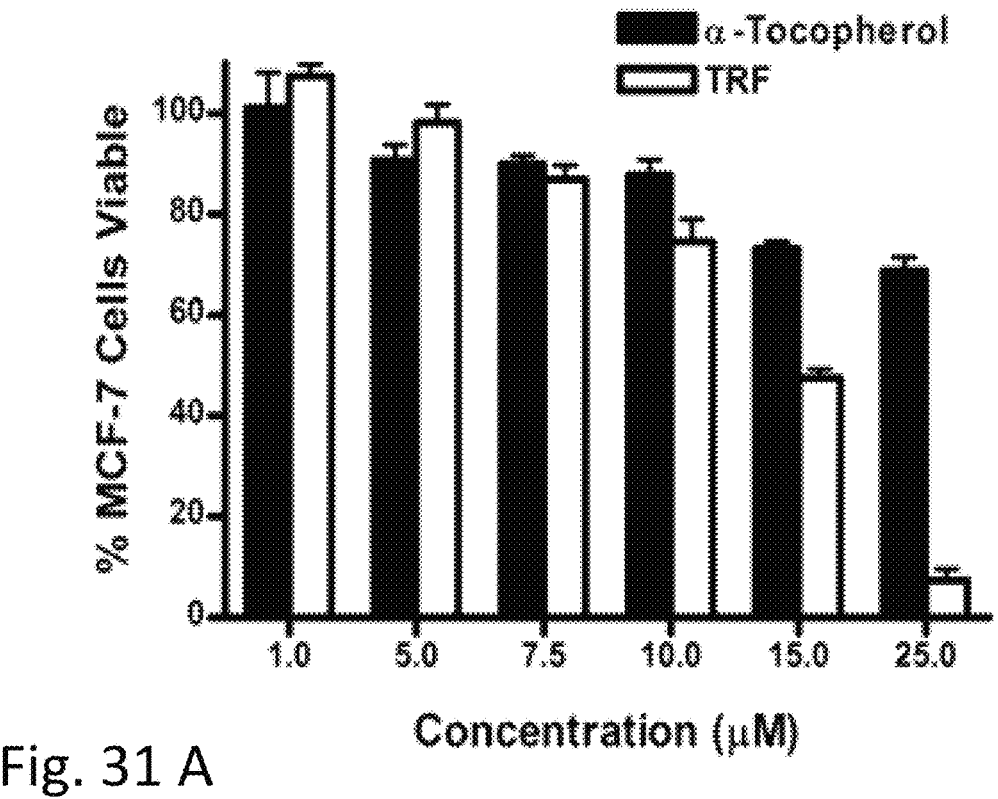
FIGS. 31A and 31B are plots of anti-proliferative impacts of α-tocopherol and TRF against MCF-7 and SW-620 cells respectively.
Figure 31:
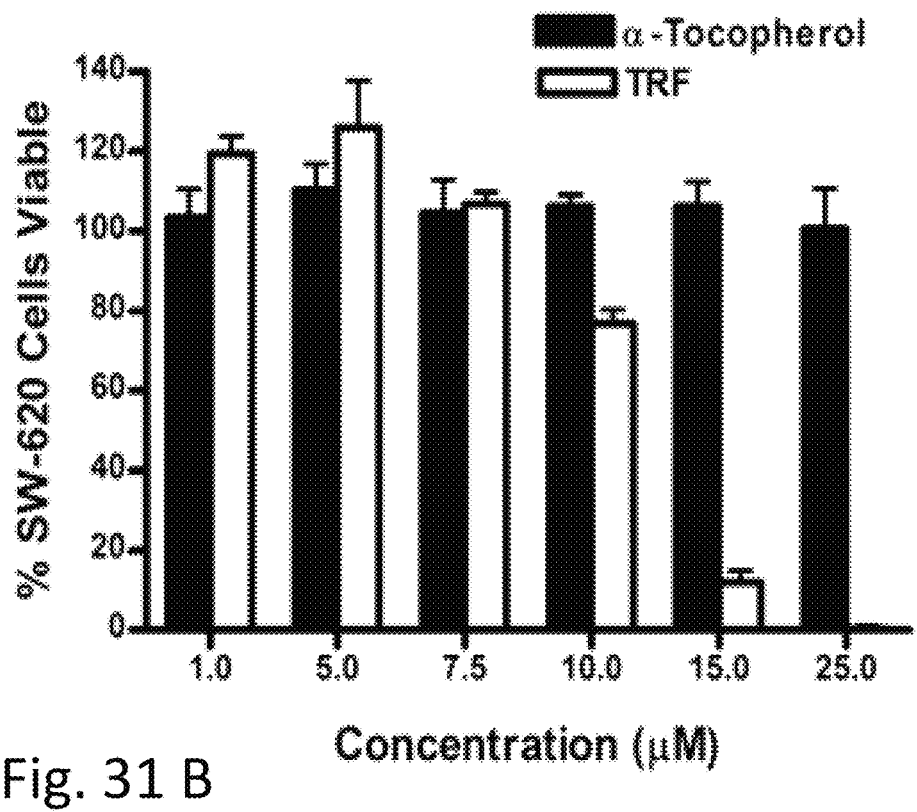

FIGS. 31A-31B show the anticancer effects of TRF and tocoppherol loaded emulsions on (A) MCF-7 (human mammary adenocarcinoma) and (B) SW-620 (human colon adenocarcinoma) cells. Cells were initially plated at a density of $1 \times 10^4$ cells/well (6 wells/group) in 96-well plates and treated with formulations supplemented with serum-free medium. Viable cell number was determined by measuring luminescent ATP using CellTiter-Glo® reagent. Vertical bars indicate the mean cell count +SEM (n=6).

TRF fortified lipid emulsions exhibited a dose dependent inhibition in cell growth and were found to significantly reduce cell viability at concentrations as low as 15 µM against both cell lines. The $IC_{50}$s of TRF lipid emulsions were 14 and 12 µM against MCF-7 and SW-620, respectively. The $IC_{50}$ sof the tocopherol lipid emulsion were approximately 69 and 78 µM against MCF-7 and SW-620, respectively. The significant difference in activity between the two emulsions confirms the anticancer activity of tocotrienol and the potential benefits of this type of emulsions in cancer therapy.

Example 20

In prophetic embodiments related to the tocotrienol and TRF emulsions described herein, tocotrienol or TRF may be replaced by one or more chemically modified derivatives of tocotrienol shown to possess beneficial therapeutic properties sometimes referred to herein as (a) "tocotrienol derivative(s)." Tocotrienol, TRF and such tocotrienol derivatives are characterized together herein as "tocotrienol based composition(s)." Tocotrienol based compositions have either tocotrienol or derivatives of tocotrienol as the predominate vitamin E species.

There are, of course, other alternate embodiments which are obvious from the foregoing descriptions of the invention, which are intended to be included within the scope of the invention, as defined by the following claims.

We claim:
1. A composition of matter comprising:
   a. a quantity of vitamin E;
   b. a glycerol ester; and
   c. a polyoxyethylated triglyceride;
   d. wherein the composition of matter is sufficiently homogenized to perform as a self-emulsifying drug delivery system;
   e. wherein the quantity of vitamin E is at least 15 weight percent of the composition of matter;
   f. wherein the quantity of vitamin E is at most 55 weight percent of the composition of matter;
   g. wherein the composition of matter is configured such that it completely emulsifies upon dissolution in water; and
   h. wherein the composition of matter is sufficiently homogenized to create an aqueous emulsion having an intensity-weighed mean droplet size of less than 700 nm upon dissolution in water.

2. The composition of matter of claim 1 wherein the polyoxyethylated triglyceride is between 18.3 and 34.6 weight percent of the composition of matter.

3. The composition of matter of claim 1 wherein the polyoxyethylated triglyceride is polyoxyethylated castor oil.

4. The composition of matter of claim 1 further comprising ethanol.

5. The composition of matter of claim 1 wherein the polyoxyethylated triglyceride is between 18.3 and 34.6 weight percent of the composition of matter and wherein the polyoxyethylated triglyceride is polyoxyethylated castor oil.

6. The composition of matter of claim 1 wherein the majority of the quantity of vitamin E is tocotrienol.

7. The composition of matter of claim 1 further comprising a triglyceride of caprylic or capric acid.

8. The composition of matter of claim 1 further comprising a triglyceride of caprylic or capric acid wherein the triglyceride of caprylic or capric acid is at least 3.2 weight percent of the composition of matter and at most 6.1 weight percent of the composition of matter.

9. The composition of matter of claim 1 wherein the glycerol ester is between 18.3 and 34.6 weight percent of the composition of matter.

10. The composition of matter of claim 1 further comprising a triglyceride of caprylic or capric acid; wherein the majority of the quantity of vitamin E is tocotrienol; and wherein the glycerol ester is between 8.4 and 34.6 weight percent of the composition of matter.

11. The composition of matter of claim 1 wherein the quantity of vitamin E is between 50 and 70 weight percent of the composition of matter.

12. The composition of matter of claim 1 wherein the quantity of vitamin E is between 17.5 and 55 weight percent of the composition of matter.

13. The composition of matter of claim 1 wherein the polyoxyethylated triglyceride is polyoxyethyleneglycerol 35 triricinoleate.

14. The composition of matter of claim 1 wherein the polyoxyethylated triglyceride is about 18.3 weight percent of the composition of matter.

15. The composition of matter of claim 1 wherein the glycerol ester is a polyglycolyzed glyceride.

16. The composition of matter of claim 1 wherein the polyoxyethylated triglyceride is polyoxyethyleneglycerol 35 triricinoleate; and wherein the glycerol ester is a polyglycolyzed glyceride.

17. The composition of matter of claim 1 wherein upon mixing of the composition of matter with water a resulting emulsion has an intensity-weighed mean droplet size of less than 500 nm.

18. The composition of matter of claim 1 wherein upon mixing of the composition of matter with water a resulting emulsion has an intensity-weighed mean droplet size of less than 300 nm.

19. The composition of matter of claim 1 wherein upon mixing of the composition of matter with water a resulting emulsion has an intensity-weighed mean droplet size of less than 250 nm.

20. A composition of matter consisting essentially of:
   a. 50 weight percent vitamin E;
   b. 29.5 weight percent polyoxyethylated triglyceride; and
   c. 20.5 weight percent glycerol ester;
   d. wherein the composition of matter is sufficiently homogenized to perform as a self-emulsifying drug delivery system;
   e. wherein the composition of matter is configured such that it completely emulsifies upon dissolution in water; and
   f. wherein the composition of matter is sufficiently homogenized to create an aqueous emulsion having an intensity-weighed mean droplet size of less than 700 nm upon dissolution in water.

* * * * *